(12) United States Patent
Péclat et al.

(10) Patent No.: US 6,758,837 B2
(45) Date of Patent: Jul. 6, 2004

(54) LIQUID DELIVERY DEVICE AND METHOD OF USE THEREOF

(75) Inventors: Christian Péclat, Neuchâtel (CH); Emmanuel Gremion, Echarlens (CH); Alain Saurer, Neuchâtel (CH); Daniel Siegfried, Bern (CH); Stefan Käser, Aarau (CH); Beat Villiger, Reinach (CH); Hans Himbert, Bromma (SE)

(73) Assignee: Pharmacia AB, Stockholm (SE)

( * ) Notice: Subject to any disclaimer, the term of this patent is extended or adjusted under 35 U.S.C. 154(b) by 152 days.

(21) Appl. No.: 10/071,825

(22) Filed: Feb. 7, 2002

(65) Prior Publication Data

US 2002/0161344 A1 Oct. 31, 2002

Related U.S. Application Data

(60) Provisional application No. 60/328,551, filed on Oct. 11, 2001.

(30) Foreign Application Priority Data

Feb. 8, 2001 (SE) .............................................. 0100418

(51) Int. Cl.$^7$ ....................... A61M 35/00; A61M 37/00; B65D 88/54; B65D 83/00
(52) U.S. Cl. ....................... 604/295; 604/151; 222/401; 222/325
(58) Field of Search ................................ 604/294–302, 604/133–134, 140–141, 151; 222/95, 209, 401, 628, 325–326, 136, 144, 420–422

(56) References Cited

U.S. PATENT DOCUMENTS

| 2,642,062 A | | 6/1953 | May | | |
| 3,419,007 A | | 12/1968 | Love | | |
| 3,653,592 A | * | 4/1972 | Cowan | ....................... | 239/692 |
| 3,800,212 A | * | 3/1974 | Branco et al. | ................. | 322/28 |
| 3,982,347 A | * | 9/1976 | Brandl et al. | ................... | 42/84 |
| 4,111,200 A | * | 9/1978 | Sbarra et al. | ................ | 604/298 |
| 4,564,360 A | | 1/1986 | Young et al. | | |
| 4,585,439 A | | 4/1986 | Michel | ................ | |
| 4,668,220 A | * | 5/1987 | Hawrylenko | ................ | 604/155 |

(List continued on next page.)

FOREIGN PATENT DOCUMENTS

| FR | 1538565 | 7/1967 |
| WO | WO 8809187 | 12/1988 |
| WO | WO 9600050 | 1/1996 |
| WO | WO 9606581 | 3/1996 |
| WO | WO 9855059 | 12/1998 |
| WO | WO 0108732 | 2/2001 |

Primary Examiner—Glenn K. Dawson
Assistant Examiner—Linh Truong
(74) Attorney, Agent, or Firm—Dinsmore & Shohl LLP

(57) ABSTRACT

A device and use method for ejecting a liquid stream towards an eye, the stream moving from a proximal position towards a distal position, the device comprising a) a housing, b) a container for the liquid, c) at least one opening arranged for ejection of the stream and being in fluid communication with the container, d) a pump mechanism operable to deliver at least part of the liquid from the container through the opening to form the stream and e) an eyecup with a contact surface arranged for contact with the eye or its facial surroundings. The eyecup is arranged movable with respect to the opening or housing between at least two positions i) an active position with said eyecup contact surface at a defined safety distance to the opening and ii) a rest position with the eyecup contact surface at a position more proximal than in the active position and a sensor is arranged to allow discrimination between the positions. The pump mechanism may include a pump driver able to store cocked energy for driving the pump mechanism and at least one activation mechanism may be present and operable to initiate the device for the liquid delivery, whereby a driving mechanism is arranged to transform manual or stored energy both i) into cocked energy of the pump driver and ii) into direct or stored energy for operation of the activation mechanism.

42 Claims, 11 Drawing Sheets

Standby Position

U.S. PATENT DOCUMENTS

| | | |
|---|---|---|
| 4,950,246 A | 8/1990 | Muller |
| 4,952,212 A | 8/1990 | Booth et al. |
| 4,968,299 A | 11/1990 | Ahistrand et al. |
| 5,026,343 A | 6/1991 | Holzer |
| 5,201,726 A | 4/1993 | Kirkham |
| 5,354,287 A | 10/1994 | Wacks |
| 5,360,410 A | 11/1994 | Wacks |
| 5,368,582 A | 11/1994 | Bertera |
| 5,399,163 A | 3/1995 | Peterson et al. |
| 5,480,381 A | 1/1996 | Weston |
| 5,501,673 A | 3/1996 | Hjertman et al. |
| 5,518,179 A | 5/1996 | Humberstone et al. |
| 5,535,746 A | 7/1996 | Hoover et al. |
| 5,607,410 A | 3/1997 | Branch |
| 5,637,984 A * | 6/1997 | Chu .............................. 322/8 |
| 5,709,668 A | 1/1998 | Wacks |
| 5,716,338 A | 2/1998 | Hjertman et al. |
| 5,838,350 A | 11/1998 | Newcombe et al. |
| 6,547,755 B1 * | 4/2003 | Lippe et al. .................. 604/67 |

* cited by examiner

Standby Position

Touch Foil Position

Peel off position

Hammer: Injection position

Start index position

Open cover position

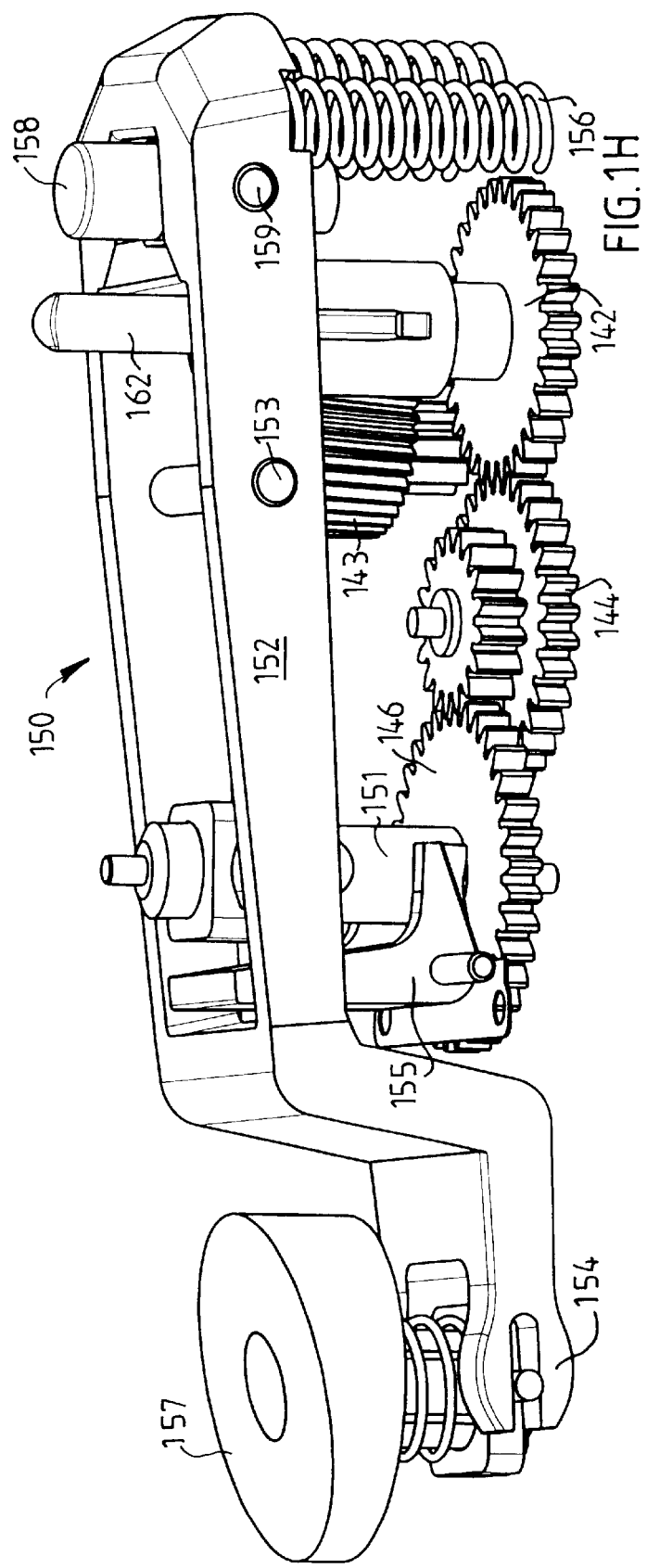

LIQUID DELIVERY DEVICE AND METHOD OF USE THEREOF

RELATED APPLICATION

The present application claims priority under 35 U.S.C. §119 of U.S. application Ser. No. 60/328,551 filed Oct. 11, 2001.

TECHNICAL FIELD

The present invention relates to devices and methods for ejecting a liquid stream, in particular towards an eye, the stream moving from a proximal position towards a distal position, the device comprising a) a housing, b) a container for the liquid, c) at least one opening arranged for ejection of the stream and being in fluid communication with the container, d) a pump mechanism operable to deliver at least part of the liquid from the container through the opening to form the stream and e) an eyecup with a contact surface arranged for contact with the eye or its facial surroundings. The pump mechanism may include a pump driver able to store cocked energy for driving the pump mechanism and at least one activation mechanism may be present and operable to initiate the device for the liquid delivery.

BACKGROUND

Devices for ejection of liquid streams may have many utilities. In the medical area typical applications include injection or infusion, treatment of a body cavities, intrapulmonary delivery or treatment of the body surface such as topical treatment. For reasons to be explained, aspects of the present invention have special utility in ophthalmology and especially in liquid treatment of and eye. For convenience and unless otherwise indicated the invention will be described in terms of this application although-aspects of the invention has broader utility.

Devices for delivery of fluids, and in particular liquids, to the eye have been used since long for a great variety of purposes. The common eye bath for comfort, refreshment or rinsing may comprise a cup of anatomically adapted design for immersion of the eye. Delivery of large liquid amounts, usually by spray devices, has also been used in eye washes for example in emergency situations. The present invention is mainly concerned with devices suitable for administration of relatively small amounts of fluids to the eye and also devices of sufficient convenience in handling to facilitate or encourage frequent use, also in self-administration situations. A common application is the administration of medical to the eye. Typically the medical preparation has to be delivered in a fairly well defined volume to assure a specified dose to be delivered or absorbed. A large surplus cannot be allowed due to improper physiological effects from absorbency in non-target tissues or drainage of excess amounts through the tear channel into the throat cavity or the inconveniences caused by overflow on face and clothes. Also price considerations apply for expensive medications. As an example, the treatment of glaucoma requires frequent daily administrations of e.g. prostaglandins, beta-blockers or other expensive active ingredients, all having other then the desired pressure relieving action when absorbed by other body tissues than the eye. Moreover, proper administration of small amounts is complicated by the fact that the active ingredients cannot enter the eye but through the limited area of the cornea. Although the device to be described herein can be used with any fluid for any purpose, for convenience the invention will mainly be described in terms of medical applications.

The circumstances mentioned place severe demands on a device for the general purposes stated. The necessarily small preparation amount has to be positioned with great care in the eye not to invoke the dosing, overflow, side-effect and targeting errors mentioned. Typically also secondary steps have to be mastered, such as initiation steps and control of device status and preparation condition.

These demands can be met also when using the simplest delivery devices when in the hands of a skilled operator who also may initiate medically relevant corrective measures in case of accidents and malfunction. Also when using sophisticated devices for example in a hospital environment. However, a general treatment trend is to place administration responsibility on the patients themselves, also in the case of child, elderly and disabled persons. In long-term treatment the patient often develop a certain skill but less frequent administration schemes also exist, often including situations of emergency or patient imbalance. Other unique problems in patient self-administration, as compared to assistant operated administration, is that less suitable and often strained body positions are required and that apprehended or experienced pain or discomfort may interfere with the medically desirable action pattern. In summary, especially the self-administration requires more sophisticated devices to facilitate the injection procedure and avoid or reduce risks for mistakes. Patients dependent on daily or occasional administrations also have a legitimate need for convenience and devices discrete enough to be brought around in daily life. Yet it is desirable that such sophistication and convenience is kept simple and inexpensive to allow for widespread distribution and inclusion also in disposable devices.

Prior art devices have only to a limited extent been able to fulfill the demands stated. Devices with manually controlled pump mechanisms have been proposed, for example in WO 98/55059 and U.S. Pat. No. 5,607,410 having features for convenient use or compact transport form respectively. However, such devices, directed to multiple-dose containers have no specific means for self-control, e.g. in respect of initiation steps or liquid status. For some purposes it is desirable to replace manually operated pump mechanisms with some kind of automated operation, typically involving release of stored energy, e.g. for controlled initiation, triggering, forces, speed, reset or sequencing. Also special demand may be posed by requirements for high liquid speeds. Medical devices of this kind are for example auto-injectors, where liquid injection takes places automatically after triggering, and jet-injectors where penetration takes place by use of liquid speed instead of by use of a needle. In eye treatment fairly rapid liquid streams have been proposed for the purposes of delivering the liquid fast enough to beat the blink reflex and also to enable delivery of very small doses, smaller than a gravity delivered drop, by ejection of controlled amount of liquid from a pressurized chamber through a narrow orifice. Devices of this kind are described in for example in WO 96/00050 for multiple dose containers and in WO 96/06581 and our co-pending application PCT/SE00/01514 for single dose containers. The disclosed proposals of this kind are not optimized for use as portable or handheld devices, neither in respect of convenience features nor in respect of suitability for further automation.

Accordingly there is a continuing need for simple and inexpensive ejection devices able to assist the user in the various handling steps involved, preventing or ameliorating mistakes and offering an ergonomic, convenient and non-traumatic product, especially useful for patients under self-administration. Although the present invention may have a more general utility, it will mainly be described against this background.

SUMMARY OF INVENTION

A main object of the present invention is to provide an liquid delivery device meeting the general demands described herein-above better than hitherto known devices. A more specific object is to provide such a device suitable for portable or hand-held use. Another object is to provide a device convenient in use and suited for self-treatment situations. Still another object is to offer a device useful for mechanized, rather than manual, operation of its liquid pump mechanism. Yet another purpose is to offer a device having arrangements for initiation and/or control steps. A further object is to provide such a device suitable for automation or motorization of its functions. Yet another object is to provide a motorized device providing energy and/or force economy. Still another object is to provide a device suitable for high speed delivery of liquid. Another object is to provide a device compatible with multi-dose or single dose containers. A further object is to provide a device suitable for use with one or several replaceable single-dose or multi-dose containers. Still another object is to provide devices as of suitable secondary properties, outside the immediate treatment situation, such as recharging, initiation, control, cleaning, handling and manufacture. Yet another object is to provide devices as above suitable for liquid delivery to an eye. A farther object is to provide an eye treatment device suitable for convenient and precise delivery, especially of small liquid volumes. Further objects are to offer methods for operation of such devices and/or methods for delivery corresponding to such devices.

These objects are reached with the characteristic features set forth in the appended patent claims.

According to one aspect of the present invention the device is arranged for liquid delivery to an eye and comprises an eyecup arranged to define a given relationship between the opening and the eye. By making the eyecup movable between at least two position, an active position providing a safety distance between the opening and the eye and a position closer to the opening it is e.g. possible to make the device more compact in its not active state, improving portability, and with increased space between device and face in operation, improving its hand-held characteristics and facilitating self-treatment. Making the variation in relation to the opening facilitates its precise orientation, of importance for delivery precision, and its integration with the housing and pump mechanism, e.g. obviating the need for long conduits in between, being more compatible with high pressure delivery. If a sensor or other arrangement is used to discriminate between the positions it is possible to adapt the device functions accordingly, e.g. to generate signals, activating electronics or mechanics, locking the device etc. Without sacrifices in other respects it is possible to add further positions for the eyecup, e.g. for reset, recharging etc. A movable arrangement is also easily extended into a fully removable arrangement, e.g. for facilitating cleaning or allowing replacement or selection between different eyecup shapes or sizes. The mobility is compatible with added functionality where the movement as such, not only the eyecup position, is critical. For example, the device may be active to move the eyecup to the active position when initiation or control has been successfully concluded or the device may be a passive receiver of movement input, e.g. by using the movement for arming or cocking mechanisms in the device. It is clear that the functionality outlined may serve to facilitate automation and motorization capabilities in the device. Similar advantages can be obtained in other applications than eye treatment if application specific movable parts are made movable in corresponding manners.

According to another aspect of the present invention the device comprises an activation mechanism operable to initiate the container or opening for the liquid delivery and a driver arranged to transform manual or stored energy both into cocking energy of a pump driver for the pump and into energy for operation of the activation mechanism. Use of a cocking arrangement for the pump driver means that the user can be relieved from operating the pump and can be used to improve the timing, profile and targeting precision of the ejection and allows any pump force, container pressure or liquid speed to be generated. Use of the same drive mechanism also for initiation facilitates handling in manual devices and reduces complexity in automated devices. Initiation steps are common in delivery devices and may for example include moving a new single-dose container into the ejection site, opening of a sealed opening, mixing of preparation precursors, breaking of rupturable walls or safety parts, dose setting, de-aeration of container content, arming or release of safety arrangements etc. The invention is compatible with any such initiation step or combination of such steps. The repertoire of available initiation actions also makes the device compatible with single-dose or multi-dose containers, with single or plural container arrangements and with fixed or replaceable such containers. Peak force or energy requirements can be reduced if the two transformations are separated in time or sequence. The same applies if two or more initiation steps are similarly separated. The arrangement is compatible both with that the driving mechanism directly operates the activation mechanism or that the driving mechanism provides stored energy to a cocked state for the activation mechanism. The principles outlined improves use convenience by reducing the necessary handling steps. They also add to safety by allowing control steps to be included and controlled sequencing between steps. Mechanization and automation of the device is facilitated by the combined operational actions and possibilities to reduce force and energy requirements. For similar reasons the device mechanism can be made simpler and less bulky, improving its portability and hand operated properties.

Further and more specific objects and advantages will be evident from the detailed description below.

DEFINITIONS

Unless clearly referring to a specific detail, as used herein "system" shall be understood to refer to the principles of the invention generally, whether described, claimed, exemplified or implemented as one or more devices/arrangements, methods, uses or combinations thereof.

In the absence of explicit statements or obvious conditions to the contrary, as used herein expressions like "comprising", "including", "having", "with" and similar terminology shall not be understood to be exclusively restricted to recited device elements, composition compounds/components or method steps but shall be understood to allow for the presence of further elements, compounds/components and steps as well. It shall be understood to cover any device element in integral, subdivided or aggregate forms and expressions like "connected", "attached", "arranged", "applied", "between" and similar terminology shall not be understood to cover exclusively direct contact between the recited elements but shall be understood to allow for the presence of one or several intervening elements or structures. The same applies for similar expressions when used for description of forces and actions. Similarly, in the absence of explicit statements or obvious conditions to the contrary, such expressions shall be understood to include composition compounds/components in any physical or chemical aggregation or mixture, with possible intervening compounds/components, or state of aggregation as well as method steps in any time sequence.

Also as used herein, positional and directional statements for both the container and the delivery device, such as "axial", "distal" and "proximal", "front" and "rear" and "forward" and "rearward", shall be understood with reference to the liquid delivery direction, with respect to which a line centered in the container opening and drawn along the main or average delivery direction shall be regarded as the system "axis" along which axis the liquid is delivered in the forward direction.

Also as used herein the concept "manual" in connection with force or energy applied to the controls of the device shall be understood to mean that the operator applies, directly or indirectly, the force or energy in a manner controlling the procedure under consideration. It shall be understood to include servo arrangements in which force or energy from another source than the operator, e.g. stored energy in a spring or gas or supplied energy, is used in fill or in part in assisting driving of the procedure as long as action of the operator determines the proceeding, although servo assistance is mostly not needed or preferred. In contrast to a "trigger" action, which may be an on/off action, the manual action bears, at least partly or over a limited range, a function relationship to position in the procedure affected.

DETAILED DESCRIPTION

General

The device described herein may be used for a variety of purposes within and beyond the medical area and for any type of preparations, such as chemicals, compositions or mixtures, in any container and delivered for any purpose. For reasons outlined the system have certain special values in connection with medical delivery devices where also the design constraints are more severe than in most other applications. For convenience the invention will be described in terms of this application.

Normally the material to be delivered is a fluid and preferably a liquid, including materials behaving as liquids such as emulsions or suspensions. These observations relate to the final preparation whereas other components, notably solids, may be present before final preparation. The nature of container content shall also be understood to include medical in broad terms and to embrace for example natural components and body fluids pre-filled or drawn into the container although most commonly the medical is factory prepared.

The principles of the present invention may be used for delivery devices or systems in broad terms. A delivery conduit from the device may be an infusion channel or any conducting arrangements such as a tube or catheter, a needle or cannula or a needle-less system based on liquid jet or a drop gun or spray with or without gas propellant. The container content material shall be deliverable by use of a delivery mechanism, also referred to herein as a pump or pump mechanism, and any material fulfilling this requirement can be used. Normally the material is a fluid and preferably a liquid, including materials behaving as liquids such as emulsions or suspensions. These observations relates to the final preparation whereas other components, notably solids, may be present before final preparation.

The invention may be applied to delivery devices in stationary or permanent set-ups. For reasons explained the invention give special advantages in delivery devices for ambulatory purposes, especially those being autonomous with on-board energy storage, motor and processor arrangements and in particular small hand-held devices of truly portable nature.

The Housing

The device housing shall be understood in general terms and mainly represents the point of reference, unless otherwise indicated, for movements and also the point of reference for forces applied by actuating arrangements performing said movements, whereat the force is applied between the housing and the moving or gripped part. Movable parts may be present in the pump arrangements or e.g. in parts performing mixing, autopenetration, needle ejection and retraction etc. The minimum functional requirement is that the housing offers a support or platform for the movable parts and the actuating arrangements providing the movements and forces. In the present context such movable parts may be present in the pump mechanism, its driver and cocking arrangements as well as in the initiation arrangements and their activation mechanisms. As in common practice, however, it is preferred that the housing forms a container at least partly embracing the parts and preferably also to such an extent that only the features designed to be controlled or monitored by the operator are externally exposed. In the present context such exposed parts may include a manually operated button for performing or triggering ejection, a door to a container seat for easy replacement, a display for messages to the user etc.

The Container

The container part shall be understood in broad sense and may take a variety of forms such as any kind of tube, vessel, flexible bag, vial, ampoule, cartridge, carpoule, syringe body etc. Common container materials such as glass or plastic can with preference be used. The container may be an integral or composite structure, such as including an outer casing or any other multipart construction for closures, fixtures, protection etc., and whenever used herein "container" shall be understood to include any auxiliary part present. The container may be integral with the housing, e.g. for use in disposable devices, when the container is refillable or when the container is part of the pumping system repeatedly drawing the preparation to be injected from an external source or channel before each injection stroke. The container may also be separate, e.g. for allowing replacement in case of disposable prefilled containers, for simple sterilization or scrapping in case of change of content type or patient. As known per se more than one container may be present, e.g. in case it is desirable to perform a mixing before injection, mixing during injection when drawing a part volume from each container or in case of sequential injection of different components.

The container has at least one opening, also referred to as an orifice, through which the medication pass during the main delivery operation of the device, either from the container interior to the surrounding for e.g. administration of the medical to the patient or to the container in case of aspiration of body fluids or at preparation steps such as filling, mixing or dissolution in the container, during which operations the opening need to be present. It is possible and even in many situations preferred that certain device operations, such as initiation, takes place before communication has been established and the opening requirement shall then be considered satisfied by the preparation arrangements for creating the communication such as the presence of a removable closure or a pierceable or rupturable part on the container itself as in the case of an ampoule or bag or a specially designed part as in case of penetrable membranes or septum. All communication may take place through one opening, for example both medical passage and pressure equalization in a rigid container or by delivery from a container which is flexible or has a movable or deformable part but nothing prevents that farther openings are provided for similar purposes, which can be identical to the at least one opening but which can be entirely different and for example be adapted for another purpose of e.g. infusion or syringe type with a movable wall or piston.

The container may be a simple bottle, vial or bag in case the delivery device is arranged to withdraw, continuously or intermittently, metered amounts therefrom for delivery as defined. Often, and especially in connection with self-administration, the container type is more elaborate and is commonly in the form of a cartridge, being the container part of a syringe type of delivery system, which may be still more elaborate in the case of multichamber cartridges. Cartridge type containers shall be further described as they generally require additional initiation or control steps for which the principles of the invention with preference can be exploited.

A cartridge for the present purposes may generally be said to include a vessel having a front part and a rear part defining a general cartridge axis, an outlet for the preparation arranged at the front part and at least one movable wall arranged at the rear part, a displacement of which wall causes the preparation to be moved towards or expelled through the outlet. Vessel shape and movable wall have to be mutually adapted. The vessel may be designed most freely when the wall is a flexible or oversized membrane or diaphragm able to adapt by movement or reshaping to vessel internal surfaces, in which case a fluid cushion or resilient material may be needed between the wall and piston rod to smooth out applied pressure. Preferably, however, the vessel has a substantially constant internal cross-section, with a similarly constant vessel axis, between front and rear parts giving a generally tube-shaped vessel, and most preferably the cross-section is of the common circular type giving a substantially cylindrical vessel. The movable wall is then preferably a substantially shape-permanent, although possibly elastic, body sealingly adapted to the internal vessel surface and preferably of the plunger type having sufficient length to self-stabilize against tumbling during travel along the vessel. The front part outlet may be of any known design and directed laterally for best access in certain applications, frontal but non-coaxial with vessel axis or most commonly arranged frontal and coaxial. The outlet may be integral with the vessel or in a conventional manner the cartridge front end may be provided with an attachment therefore and before connection be provided with a breakable or penetrable sealing.

Generally the described cartridges need several kinds of initiation actions, dependent on a displacement of the movable wall, to reset the device and make possible repeated and reproducible dosing meeting high precision demands. In its first movement the movable wall may need an extraordinary break-loose force after storage to overcome both internal reshaping resistance and an increased wall friction due to adherence or depletion of lubricant in contact points. Also in relation to the weaker regular injection force, elastic and inelastic deformations and tolerances have to be evened out in the movable wall, cartridge shell, outlet attachments etc. The preparations themselves may have compressible inclusions such as gas vesicles. Deaeration and preejection is needed to remove gas in the vessel compartment and fill out spaces for example at the front sealings, outlet attachments and the interior of the outlet devices or needles.

Dual or multi chamber cartridge types are known e.g. for preparations demanding a mixing of two or more components or precursors before administration. The components are kept separated by one or more intermediate walls of different known designs, which walls divide the vessel into several chambers, sometimes placed parallel along cartridge axis but most commonly in stacked relationship along the axis. Unification of the components may take place by breaking, penetrating or opening a valve construction in the intermediate walls, for example by introducing a pin or needle through the cartridge front, through or at the rear movable wall or by means at the cartridge exterior (compare e.g. WO 93/02720). In another known design the intermediate wall or walls are of the plunger type and flow communication between the chambers is accomplished by moving the plunger to a by-pass section where the interior wall has one or several enlarged sections or repeated circumferential grooves and lands in a manner allowing by-flow of rear chamber content into front chamber at displacement of the rear movable wall (compare e.g. U.S. Pat. No. 4,968,299 or WO 93/20868 and WO 95/11051). The chambers may contain gas, liquid or solids. Generally at least one liquid is present. Most commonly in pharmaceutical applications only two chambers are present and typically contains one liquid and one solid, the latter being dissolved and reconstituted during the mixing operation.

Initiation of the multi-chamber type cartridges requires all the general type steps described, although in aggravated form due to the additional walls and spaces present. In order to provide for efficient mixing generally a mixing space has to be allotted in addition to the space occupied by the component volumes. Powdered components in bulk form also require the extra space contained in interstices between particles. The mixing step may produce foam or gas inclusions requiring space to settle out. Plunger type intermediate walls generally have to be displaced at least their own length to reach the non-sealing site in the by-pass. In total multi-chamber type cartridges require long movable wall strokes in the initiating step, both for mixing and subsequent deaeration, and benefit in a particular way from the advantages of the current invention.

In general the containers exemplified can be used either for single or multiple doses to be ejected. In medical applications multiple dose arrangement often involves the risk of contamination or loss of sterility of the container content after opening and first use, which may require preservatives in the preparations. These problems can be avoided with single dose containers which are opened in connection with the ejection operation and then discarded. For cost reasons the simple and cheap single dose containers have been proposed having an opening and at least one wall which is soft or deformable so that the container content can be pressurized by squeezing or impacting the deformable part. Various pressurizing directions can be used such as perpendicular relative to the opening axis although it is often preferred to use a direction parallel and preferably co-axial with the opening axis in the forward direction. Such containers have been proposed for various delivery purposes, e.g. for needle injection as exemplified by FR 1538565, for penetrating jet injection as exemplified by U.S. Pat. No. 2,642,062, U.S. Pat. No. 3,419,007 and U.S. Pat. No. 5,026,343 and for eye treatment as exemplified by WO 96/06581 and our co-pending application PCT/SE00/01514 mentioned in the introduction. Containers of this kind can be used for the present purposes and the most preferred design is that described in said co-pending application. Such a container can be said to comprise a front wall having or surrounding a cavity corresponding to the form of an open vessel, an opening in the front wall adapted for ejection of the liquid from the container, optionally a sealing over the opening adapted for temporary use, and a rear wall closing and sealing the open part of the front wall vessel to confine a space for the liquid in the container, the rear wall running at least partially perpendicular to the container axis and being displaceable or deformable for movement towards the opening to pressurize the container liquid. The front wall is substantially rigid in relation to the rear wall, that the rear wall before pressurizing the container is substantially flat or substantially single-curved and that the rear wall is deformable under stretching to substantially fill out the container cavity. The pump mechanism for such containers may include a ram that press or impact on the soft or deformable wall, to be further explained below.

Although the above considerations apply to individual containers for single and discrete use it is preferred to provide for multiple container units or packages. This can be done by joining several individual container into multiple structures, e.g. by flexible joints to allow structures that can be bent, folded or rolled. Preferably, however, the multiple container package is a substantially rigid and self-bearing structure, among others giving advantages in connection with the delivery device. A rigid structure can be obtained by joining the individual containers by rigid joints but a preferred way is to utilize the rigidity of the front wall as mentioned by providing an enlarged front wall structure and provide several cavities in the structure, among others facilitating manufacture of multiple containers and allowing a smooth and non-complicated exterior. By utilizing the feature of making the front and/or rear surface of the front wall structure flat or single-curved the attachment of films over these surfaces is further simplified, especially if the container surfaces lies in the same plane since an undivided sheet material can then be attached to several, and preferably all, of the individual containers of the structure, e.g. a common foil attached as rear wall to the rear surface of structure or a common peel sheet over the container openings at the front surface.

The overall shape of the front wall structure for multiple containers can take a variety of forms but essentially flat front wall structures give advantages in manufacture and delivery device design. The shape may for example be rectangular, square or round. The round "disc" shape has been found particularly beneficial, among others in connection with the delivery device where sequential feeding of the containers into a shoot position can be made by simple rotation in a "revolver" type manner, the absence of any particular start position facilitates handling and counting arrangements and allows for self-centering properties.

Most container types can be arranged in multiple arrangements if desired and an initiation step for any such arrangement may include the step of bringing a fresh container into an active ejection site of the delivery device or bringing the site to a fresh container position.

As indicated it is preferred to temporary seal the container opening or openings before actual ejection of the liquid in order to maintain a fully sealed container. The seal should be broken or removed immediately before use. Although a manually or pressure breakable rupturable seal can be used it is often preferred to use a removable seal in order to avoid any particle release from the seal, to have a fully foreseeable dynamic behavior and allow use of more reliable thick or strong layers. Generally a seal can be formed integral with the front wall, e.g. by molding so as to leave a membrane of material somewhere in the opening duct. Preferably, however, a separate peel layer is provided for removal prior to ejection, and preferably attached to the front surface of the front wall. It is preferred to avoid glue and adhesives and preferably some form of welding is used, as by ultrasonic or heat. In order to facilitate removal and interference with the opening area the sealing can be made to a limited area surrounding the opening. In multiple container structures it is preferred to make the layers individually removable for each container, e.g. by use of separate films, pre-cut films or separate tongues, e.g. in a star shape for a round disc. For the film material similar considerations apply as for the rear wall material, although the film need not be deformable by stretching and the demands on impermeability can be slightly reduced in view of the small opening area. An initiation step for such containers may be to remove the temporary seal before ejection.

The Opening

The opening design can vary depending on the nature of the liquid stream to be produced, e.g. an atomized spray or a concentrated stream to remain coherent or to break up into a linear stream of discrete droplets. Also the stream speed may vary from high penetrating to low impact surface delivery. Several or multiple openings can be provided, e.g. to produce a controlled shower, although for most applications a single opening is preferred. The opening geometry can be that of a simple tube, diverging, e.g. for assisting in a distributed spray, converging, e.g. for assisting in a coherent stream to be formed, or a combination, such as a venturi type of channel. In high speed applications it is generally preferred to make the duct part of the opening short in order to keep the flow friction low. Although the opening can be soft, e.g. in case of infusion tubes, precision advantages can be obtained if the opening structure is rigid. The opening in turn can be connected via a tube to the container, e.g. in case of feeding tubes, although the opening with preference also can be directly attached to the container. The opening will here be described as a termination adapted for delivery of the preparation to the target site, e.g. on or in the patient, for which purpose at least the last, frontmost, part of the conduit should be suitable for delivery to the site. Depending on the delivery mechanism used the front end may not be designed for direct contact with the target site, as in case of liquid sprays, where the front end may be an orifice or opening for positioning at a distance from the target or on the surface of the target in spite of that the true target is below the surface. In other instances the front end is designed for penetrating into the target as in case of cannulas or common needles. The channel between the front end and the rear end may be curved or bent, as for a flexible infusion tube or in an on-board permanent connection, although in many applications it is desirable that the conduit is substantially straight, as for a needle on a syringe.

The Pump Mechanism

The mechanism for delivery of medical through the container opening should basically include at least one type of pump mechanism which may have to be selected for the special kind or container and medical used. The pump mechanism may include any kind of pressure source, such as mechanical or electrolytic pressure build-up, in the container and suitable valve arrangements for control, which method can be used with virtually any kind of container and any kind of product, such as transdermal delivery through liquid jets, as exemplified by WO 94/2188, or regular tube infusion, as exemplified by WO 88/09187. Any kind of container can also be used with pumps based on peristaltic action or centrifugal action, although also for general use pumps based on controlled positive displacement are preferred and especially such pumps based on a separate cylinder and piston action, as exemplified by U.S. Pat. No. 5,480,381 for liquid jet or U.S. Pat. No. 4,564,360 for a manually operated needle based device. The common syringe type container need a specialized pumping system. Either the mechanism is adapted to act on complete syringes, having their own piston rods, by engaging and axially displacing said rod, as exemplified by the U.S. Pat. No. 4,978,335, which may be preferred when it is desired to accommodate syringes of many different types and sizes, or the mechanism has a piston rod acting more or less directly on the piston of a cartridge type container, as exemplified by WO 95/26211, EP 143.895 or EP 293.958, which can be made smaller and more adapted to portable devices. Also dual or multiple chamber cartridges can use a similar devices for its various phases, as exemplified by the WO 93/02720. Although the various pump mechanisms discussed may include mechanical arrangements for affecting the medical or a piston the arrangements, such as a piston rod, may be actuated by any known means, such as gas pressure, vacuum, hydraulics, springs or manual operation.

The mechanism may preferably include further components. The mechanism may for example include special arrangements for securing doses delivered, e.g. by direct metering of medical delivered, although it is generally preferred to utilize directly or indirectly the pump mechanism for this, e.g. by monitoring axial displacement or the rotation of a piston rod axis in a manner known per se.

The pump mechanism may also include a manual control, forming the interface between user and actual pump movement. In case of stored energy the control may take the form of a trigger, releasing e.g. a valve or a mechanical lock. In case of manual operation the control may take the form of an actuator, directly or via a link system performing the pump movement. Preferably a link system incorporates a lever arrangement which may be used to reduce the manual force applied, e.g. in case the preparation is too easily expelled or if a reduced stroke length is desired, but preferably is used to amplify the manual force or increase the stroke length for the actuator. The manual control may include common safety details such as an arming lock or command requirements making the device child proof.

Another known pump mechanism is to pressurize a small cavity of liquid by rapid and partial heating of the liquid to vapor formation or by compression by a piezoelectric element. Alternatively no pressurizing takes place but liquid adhered to a surface is thrown by vibration of the surface. Such techniques are used for delivery of small drops in rapid succession for example in ink-jet applications but have also been proposed for treatment purposes. The earlier mentioned WO 96/06581 and EP 224352 disclose piezo element and electrostatic means for eye treatment, vibration techniques are disclosed in EP 615470, U.S. Pat. No. 5,518,179 and U.S. Pat. No. 5,838,350 and bubble jet technique for eye treatment in WO 94/03135. Such pump mechanisms can be used for the present purposes, especially for delivery of small drops as sometimes desirable in eye treatment. In medical applications it is desirable to use the techniques in combination with single dose containers for example to better maintain sterility as has been explained.

When applying the present invention in connection with a pump driver working with cocked energy it is preferred to use the pump mechanisms using relatively high forces or high effects since such devices particularly well benefits from the cocking advantages, for example the possibility to use a fairly weak motor or manual input to be stored in the cocking arrangement. It is also preferred to use pump mechanisms built on a fairly simple movement pattern, such as a rotational or preferably translational movement, for example when using a ram for pressurizing the described soft or deformable containers or piston/cylinder type arrangements as in aspiration/ejection systems or pistons in syringe type devices.

Energy can be stored in the cocking arrangement in different forms such as electric, magnetic etc. although it is preferred to use pressure, e.g. in gas or hydraulic springs, and most preferably as mechanical energy, preferably mechanical springs.

Similarly the energy input to the driving mechanism can take various forms. The energy can be manual. Alternatively stored energy in any form can be used, e.g. the above said forms although the energy preferably is electric, e.g. externally delivered to the device or preferably in an on-board battery, to be transformed by any electromechanical device such as a solenoid or preferably an electric motor.

With preference a transmission can be arranged somewhere between the energy input and the pumping arrangement, e.g. to modify force, to divide energy also for initiation steps or to affect sequencing. Typically the transmission involves a gear down step from lower to higher force. This transmission may take place after the cocking mechanism energy storage but is preferably made before the storage, typically to allow the energy storage to provide higher force than the input force. Any known mechanism for the force change can be used such as a lever arrangement, a screw and nut arrangement or a gear train arrangement.

Initiation

As indicated above the various container types may need different initiation actions. For example a syringe type container may need an initial piston movement for various reasons such as mixing of precursor components. A piston/cylinder arrangement may need aspiration from a vial or feeding tube. A multiple container arrangement may need movement of a new container into an active ejection site, herein also referred to as indexing. Also removal of temporary seals may be needed, herein also referred to as peeling. All possible initiation steps shall here not be repeated.

Additional initiation steps can be said to include control steps performed to avoid malfunction or to secure that all conditions for successful operation are present. Such control steps may be check for the presence of a container in a container seat, check that the container is not already used, e.g. empty, check for the presence of a temporary seal before its removal, check for correct position of doors, closures, eyecup position etc. Such control steps can be used to prevent triggering or issue a warning unless all necessary conditions are met. As for the initiation steps mentioned above, some of such control steps can be made by microswitches or simple mechanical locks or catches but to the extent these controls need movement of parts requiring significant force or power these steps can be treated as initiation steps below.

Although the initiation steps may take place manually or by separate drive systems, for reasons outlined there are advantages in using the same drive mechanism not only for the cocking step but also for at least one initiation step. Depending on the force requirement in the initiation step a gear down force increase and possibly also a cocking arrangement for the initiation may be needed in similar manners as for the pump driver and possibly the same arrangement can then be used for both purposes. Alternatively, e.g. if the force or speed requirements are not large, the step can be driven directly without cocking arrangement and a gear up or gear down transmission or no transmission can be employed. Often the two actions need different movement characteristics or are applied to different parts, requiring at least some different parts in the driver mechanism, which often is preferred.

Independent of drive mechanism sharing, there are various alternatives for sequencing of the actions. The cocking action and the at least one initiation action, for example cocking and indexing, may be made may take place simultaneously or at least partly so, e.g. to save time between operations. Simultaneous action may either take place due to movement of the same part for both purposes, e.g. when having one cocking system for both, but preferably different pats of the driver mechanism are involved. In most instances time is not critical and it is preferred to perform the actions at least partially in sequence, e.g. to reduce the force and power requirement on the drive arrangement, of particular value in portable devices. More than one initiation step may be involved in the device use cycle, such as indexing, peeling and control, and it is then preferred to make at least two or more actions to take place in sequence to amplify the said advantages.

Some sequencing can be obtained without any active shifting action being performed by the mechanism. For example, a single movable member may carry both a plunger or ram for ejection and a peeling pin more to the front, securing its arrival before the plunger becomes operative for ejection. Different arrival times can also be obtained without the parts being located on the same part or driven by the same parts of the driver mechanism. Normally, however some shift arrangements are needed for sequencing. Typically the driver system need to be disconnected from the cocking arrangement. This can be done by locking the cocking arrangement in its cocked state and freeing the mechanism by disconnection for continued movement or by reversing motor operation. Similar actions, including different arrival times, can be used for sequencing between several initiation action.

Operation Control

Operation of the device can be said to include the necessary steps for ejection of the liquid, initiation steps and control steps when present and any interaction thereof such as sequencing as described. Control can be made entirely by software means for highest flexibility, provided the actuating arrangements present are complete enough to individually drive the various parts in their intended movements, such as separate motor means and solenoid operated locking and blocking arrangements. To secure operation in correct spatial relationship between parts, sensors or micro-switches may also be needed at critical positions for moving. Control of such parts can be made by electronics, such as a microprocessor with appropriate software.

It is often preferred, however, to provide mechanical arrangements assisting control for safest operation and may be necessary if the same motor means are to be used for different purposes, such as the above exemplified cocking and initiation steps. Mechanical shifting arrangements can easily be placed so as to be triggered by the moving parts at the critical positions. Nothing prevents use of combined software and mechanical arrangements for highest safety and operation redundancy.

Even if the main device functions are controlled mechanically it may be beneficial to include electronics for various secondary purposes, such as for issuing an alarm or to signal e.g. a warning or instruction message to the operator, e.g by light, sound, vibration or display message. Control of a display may also serve the purpose of informing the user for example about timing between administrations, remaining doses in case of multiple-dose containers or plural single-dose containers, device status etc. A processor and memory can also be used to remember time and doses administered, e.g. for control of compliance with prescription, and possibly such data can be downloaded from the device, e.g. from an on-board EPROM via an IR-link, for further processing in external equipment.

The various drives described may utilize stored energy in any known form, such as electrical, gas pressure or gas releasing, or preferably mechanical, the latter preferably in the form of elastic members such as springs. The stored energy can be transmitted to the force stated via corresponding conventional transmission arrangements, e.g. electromechanical, such as electric motors or solenoids, hydraulic, pneumatic etc. system but preferably mechanical springs are utilized.

Detail regarding use of sensors and signal processing in the device for the device will be given below in connection with description of eye cup mobility since the general principles there given is equally applicable for other parts of the device.

Uses

As indicated, features of the present invention has broad utility and can be used for numerous applications. The invention may have special utility in applications where it is desirable to replace manually operated pump mechanisms with some kind of automated operation, typically involving release of stored energy, e.g. for controlled initiation, triggering, forces, speed, reset or sequencing. The invention may also have special utility in applications having requirements for high liquid speeds. Medical devices of this kind are for example auto-injectors, where liquid injection takes places automatically after triggering, and jet-injectors where penetration takes place by use of liquid speed instead of by use of a needle. In eye treatment fairly rapid liquid streams have been proposed for the purposes of delivering the liquid fast enough to beat the blink reflex and also to enable delivery of very small doses, smaller than a gravity delivered drop, by ejection of controlled amount of liquid from a pressurized chamber through a narrow orifice. The eye treatment application will be further described below.

Eye Treatment

A preferred use of the invention is in connection with ophthalmic treatment of the eye with medical. The common administration manner is by eye drops or ointments, however, having several disadvantages. Both methods generally delivers a substantially higher amount than can be absorbed by the eye, not only resulting in dosing uncertainty and loss of expensive treatment medical but also in potential side-effects when non-absorbed preparation is drained away via the nasolacrimal duct, e.g. beta-blocking agents used in eye treatment has substantial systemic effects. Another problem is that the common administration methods tend to induce a blink reflex that may entirely destroy the treatment or at least introduce a high degree of uncertainty. Also the common methods do not provide an high degree of targeting precision, e.g. ability to hit the iris part of the eye being the penetrable part of the eye for prostaglandin. The principles used for the present invention solves these problems, among others by the possibility to deliver small amounts of liquid, actively ejected and not determined by liquid surface tension, by the possibility of delivering the liquid with sufficient speed to beat the blink reflex and by the possibility to eject a concentrated and coherent stream for precise targeting. Typical parameters for this application will be given below although the invention shall not be regarded as limited to any such exemplified parameter. A typical single dose volume for delivery to the eye can be less than 25 microliter, preferably less than 15 and most preferably less than 10 microliter. Generally the volume is at least 1, preferably at least 2 and most preferably at least 3 microliter. Since it is desirable that each container contains a single unit dose, these figures also relate to the liquid volume charged and contained in the containers, possibly allowing for some overfilling to compensate for nonejectable amounts, such as liquid remaining as wetting film or in the container opening duct, e.g. 25% but preferably no more than 10% overfilling. In addition to the liquid the container may contain other material, notably gas such as air or a purging gas such as nitrogen or noble gases, e.g. to facilitate manufacture, assist in atomizing or act as pressure buffer, although in many instances little or no gas need to be present. A suitable speed for the stream of drops or jet ejected should be a balance between on one hand enough linear momentum to traverse an air gap between opening and target, without gravity assistance, and to travel fast enough not be obstructed by blinking and on the other hand not so fast as to cause inconvenient sensible impact on the eye. The ideal speed is to some extent dependent on the drop size used but as a general rule the drops should be able to traverse at least 1 cm, preferably at least 3 and most preferably at least 5 cm through air by own momentum, incorporating reasonable distances between opening and target. A suitable lower speed limit when leaving the opening is 1 m/s, preferably at least 5 m/s and most preferably at least 10 m/s. Generally the speed is lower than 200 m/s and preferably lower than 100 m/s. A suitable drop size so defined should be sufficient not to be retarded too quickly and not to be easily redirected, e.g. to be inhaled, and preferably has a minimum diameter of 20 micron, preferably not less than 50 micron and most preferably at least 100 microns. Normally the size is less than 2000 micron and preferably less than 1500 micron. The stream may take the form of a shower or spray of atomized liquid droplets but preferably the stream is narrow and fairly coherent although even such a stream tend to break up into individual droplets after a certain time of distance. The above given values are intended to relate to spherical droplets and for multiple droplets to the weight average of particle diameters. A coherent stream tend to break up into droplets of a diameter of roughly double the diameter of the stream. Accordingly suitable opening diameters for the containers are about half the above given drop diameters or roughly between 10 and 1000 microns, preferably between 20 and 800 microns. The above considerations are fairly independent of liquid viscosity and tend to apply both for solutions and ointments.

The Eye Cup

Many of the advantages provided by the present invention are exploitable also without an eye cup part of the device, provided the operator take responsibility for device orientation and stabilization. It is preferred, however, that an eye cup part is included to relieve the operator from these responsibilities. A suitable eye cup part comprises at least a rim and a cavity.

The purpose of the rim is to give a contact between device and face for and preferably also a self-centering of the device in the intended position relative the eye. The contact can be against any part of the face such as the forehead, nose and cheek but a generally better centering is obtained if the rim make contact with the eye socket. The "rim" shall be understood in broad sense as the point or points of contact and need not be shaped as an edge or other elongated part but shall provide at least one point of contact preferably two, three or several points distributed in two dimensions for best centering. The points can with preference be shaped as one or several continuous edges and most preferably as a continuous loop. For purposes of description it is assumed that a line can be drawn so as to connect the contact points into a "contact curve", representing also theoretical face contact points not being actually contacted by the rim and in case of a closed continuous rim the contact curve and rim edge are assumed to coincide. A plane drawn to contain the contact curve forms a theoretical "contact plane". A line drawn normal to the plane forms a "contact axis" and a "contact direction" along the axis from the device towards the eye or, expressed in another way, from the cavity towards the rim. The contact axis and contact direction shall be regarded "symmetrical" if, in device related terms, they are centered within the contact curve or if, in patient related terms, they are radial to the eye ball. Suitable rim forms are known in the art and are not very critical to the invention. It is preferred to use a rim shape with left/right symmetry to make it equally usable for both eyes with a similar grip. A rim having a contact curve substantially in the form of an ellipse, adapted in size and shape to the eye socket, can for example be used. The contact plane through such a generally ellipse shaped form can be flat although frequently slightly curved along an axis parallel with the short axis of the ellipse. The rim can in a known manner with preference have eyelid retractor protrusions, preferably in the contact direction, for specific contact with at least the lower, but preferably also the upper, eyelid for the purpose of displacing and retaining the eyelids. Constructively the rim can have a soft edge for comfort and preferably a material of high friction, at least on any eyelid retractor part. The rim may be integral with the cavity part but is preferably a separate part attached, glued or fused to the cavity part for free material or color contrast selection.

The cavity serves the purpose of providing space within the contact curve boundaries for the protruding eye ball and also to secure a safety distance to the eye ball for any part in front of it, especially the orifice to be further explained. Accordingly the cavity shall be understood in broad terms for any construction meeting these objects. The cavity can be a true cup, as in known eye baths, but has no function as such and it is preferred that it has a more open design, e.g. to allow access to the orifice for opening and closing, to avoid preparation accumulation and facilitate cleaning, to allow an assistant operator to visually monitor orifice orientation and delivery, to facilitate manufacture etc. A minimum requirement is that the cavity construction provide support and attachment for the rim, e.g. a single arm or bar extending away from the rim in a direction opposite the contact direction, although two or several arms can be used for example in a cage-like design. With further details below, the eye cup shall be arranged at the orifice of the container in a manner allowing delivery of fluid to the eye and in particular within the contact curve of the rim. The relationship may depend on the delivery principle used, with special freedom at drop delivery, but generally it is preferred that the orifice is positioned behind, when seen opposite the contact direction, the contact curve and with a projection along the contact direction within said curve. The orifice can with preference point into or be arranged within the cavity, preferably with at least a fluid delivery direction component parallel with the contact direction. It is preferred that a certain safety distance is maintained between the orifice apex and the contact plane, to prevent contact with the eye ball for any foreseeable individual anatomy and to prevent patient fear for such contact, e.g. a distance of at least 5 mm, preferably at least 8 mm and most preferably at least 10 mm. The abovesaid support and attachment of the rim via the cavity construction can be made to the container or its orifice but it is preferred to attach the rim to the hand grip part, e.g. for allowing unobstructed replacement or the container.

The eyecup may include auxiliary features such as details assisting proper use and targeting, e.g. some fixation point for the eye, for example a mirror, a light etc.

Eye Cup Mobility

When using an eyecup it is preferred to arrange it movable with respect to the housing. The eyecup can preferably be movable between at least two position, an active position providing the described safety distance between the opening and the eye and a position closer to the housing, e.g. to make the device more compact in its not active state. The container opening can be fixed in relation to the eyecup, e.g. to move together with the eyecup, but in most instances it is preferred that the eyecup moves relative the opening, which is then arranged fixed with respect to the housing, certainly with maintained options for container replacement or movement of plural containers to and from an active site. The eyecup can be movable into more positions, e.g. farther away from the housing or opening than in the active position, e.g. to improve access to the eyecup or to housing parts etc. With preference the eyecup can be entirely removable from the housing, e.g. for cleaning purposes. The eyecup mobility can be in any direction as long as the above requirements are satisfied, e.g. so that the eyecup contact direction has at least a movement component along the opening axis. The movement can be purely translational or may have a rotational component, the latter preferably being obtained by a hinged arrangement for the eyecup or its attachments. It is preferred that at least some of the positions are well defined, preferably at least the active position and preferably also the rest position, e.g. by friction, snap lock, ball locks or even a full releasable locking.

It is preferred that a sensor or other arrangement is used to discriminate between the positions and preferably so that signal is issued on which the device may use for action. The signal can be able to distinguish between all possible positions in a continuous way although it is often preferred the sensor issues discrete signals for example in at least one, preferably at least two and most preferably at least three positions. The signal can be of any kind as long as it is possible to transform it into action, preferably an electromagnetic or mechanical signal.

The signal received from the sensor can be in the form of, or transformed into, an electromagnetic signal representative for the position as described. The electromagnetic signal may be based on electromagnetic radiation, such as an optical signal, but is preferably an electric signal. Many suitable components for use as sensors are designed to give such a signal output but may otherwise be inserted in a circuit securing such an output. Any inherent, integral or separate arrangements of this kind can be regarded as a converter for sensor output into the electromagnetic signal. For example, one or more micro-switches may be arranged along the eyecup translational path or along a rotational path, e.g. a cam surface arranged at a hinge axis.

Similarly the signal received from the sensor can be in the form of, or transformed into, a mechanical signal representative for the position, e.g. a part connected to the movable eyecup and in some way moving together with it. Any known transmission arrangements can be used as converter for the signal into the desired movement action with similar considerations as for the electromagnetic signals. Nothing prevents that an electromagnetic signal is transformed into a mechanical signal or vice versa or are mixed in the signal chain.

The signal so received or converted can in general terms be said to be processed in for example a processor or transmission to deliver a control signal. The control signal in turn is used to control a functional or operational component of the device. The operational components can be of any kind although some typical examples will be given below. Also the control signal can be of any nature, such as mechanical, optical etc., depending on its further use.

The control signal may be used to issue a message to the user, e.g. to warn or alert the user of an improper condition before the device is activated for delivery. The message may be a sound, a tactically sensible signal such a vibration, a visual signal in the form of a warning lamp or a more complicated message on a display etc. or any combination of such messages.

It is preferred that the control signal is used to control the basic device functions over the actions taken by the operator. The control signal may be used to enable or disable the device respectively, dependent on the proper eyecup condition. The enabling/disabling may take place by a mechanical link or by an electromechanical link, such as a relay device blocking a mechanical function e.g. a piston rod or pump mechanism. Better is to use this function in connection with devices having at least some automation means for driving the device, such as an electric motor, the operation of which may be determined by the control signal. Still better is if the device further includes processor means for control of the motor means, e.g. in order to secure proper container control, initiation, sequencing of actions, dosing, feedback of administration data etc. in which case the electromagnetic signal can be fed to the processor for further flexibility, e.g. allowing the processor to issue a motor activation control signal only when the eyecup condition is fulfilled or only when the initiation steps have been properly concluded or proper condition has been positively verified in a self-control program. An existing processor unit may here act as the processor between the electromechanical signal and the control signal.

The control signal may further be used to actually trigger the device, i.e. as soon as the sensor signals the predetermined position condition an automatic function starts. As for the enabling/disabling condition just described this triggering function can be used for purely mechanical driving means via an electromagnetic release mechanism, better together with electric motor means an most preferably with processor controlled automation in the device.

It is preferred that the device is arranged to take at least one in the initiation and ejection sequence. A preferred arrangement is to arrange so that the device can only be triggered when the eyecup is in the active position, or active state. The rest position, or rest state, can for example be used to disable triggering, put the device in a low energy consumption state or initiate a new cycle of initiation steps. A third position can be used to signal other device states than rest state or active state, for example a reset state or a change of container state and may include a step giving access to the container seat. It is also preferred that movement as such, not only the eyecup position, is critical and used for action. For example, the device may be active to move the eyecup to the active position when initiation or control has been successfully concluded or the device may be a passive receiver of movement input, e.g. by using the movement for arming or cocking mechanisms in the device.

It is clear that the above general sensor principles can be used also in devices for other purposes than the eye treatment. The operations actually enabled or triggered can then be of various nature. Preferably at least the ejection is affected, in multidose devices perhaps including mechanical but preferably electric control of the dose delivered. In jet injectors sensors can be used for contact triggering. In autoinjector type devices the autopenetration step may also be affected, preferably so that the sequence of autopenetration and autoinjection is controlled, possibly with a final needle retraction step. Autoinjectors are known which either deliver preparation also during the penetration phase or enable the injection first at completed penetration and the invention is compatible with both modes of operation. In case of multichamber cartridges with overflow or by-pass arrangements, which are known as such, the injection procedure may incorporate injection of different preparations in sequence, such as an anesthetic followed by an active ingredient or an active component followed by an rinsing component.

Device Example

Below some considerations will be given for a use example in which a device is arranged to utilize the container types described above with reference to our co-pending application PCT/SE00/01514 and especially the described multiple container arrangement in the general revolver type disc layout.

A delivery or dispenser device for such a purpose can generally be said to comprise a housing with a seat for the container or container structure, a ram movable in relation to the housing in a direction substantially axial to the container when in the seat, an actuator arrangement operative to drive the ram.

The housing should contain a seat for a container or several containers, the minimum requirements on which is that at least the container to be emptied is kept fixed in relation to the ram, preferably so that the container axis and the movement axis for the ram are parallel and most preferably coaxial with respect to the ram part to hit the container rear wall. Preferably the seat should be able to accommodate containers with the characteristics described herein. The seat preferably supports the container against forward forces from the ram and preferably also against some rearward and lateral forces. The seat preferably allows the entire rear wall surface over the cavity to be exposed to the ram and should also expose at least the opening or openings on the front side of the container not to obstruct the liquid stream, although the rigidity of the present containers do not require any heavy support. Preferably the seat is also designed to allow easy exchange of discrete containers, or sequential movement of the individual containers of a multi-container structure, into the active position of the seat, e.g. by having a track in which the structure can be moved in one or two dimensions. In the preferred embodiment of containers placed in a circle, preferably on a disc shaped structure, it is suitable to rotate the disc around a central disc axis to bring the containers into alignment with the active position, in a revolver type manner. Such indexing maneuvers may take place as an initiation step for example before or after cocking a spring for the ram ejection action. For single and in particular multiple container arrangements it is desirable that guiding arrangements are provided to secure good alignment with the ram axis in order to reach high delivery precision intended, e.g. structures provided in connection with each container on the package for cooperation with at least one corresponding locking structure on the housing, seat or preferably ram, arranged for interlocking at proper alignment. Locking therebetween can with preference be associated with a signal to assist stop in correct position, e.g. tactile or audible signal in manual operation or a mechanical or electronically detectable signal in automatic operation. Additionally it is preferred to include a counting arrangement, again manual or automatic, mechanical or electronical, designed to keep track on the number of containers used or remaining and warning for or preventing reuse of already emptied containers.

The ram may include a ram head and piston arrangement for moving the ram head along the movement axis. Although it is possible to design the ram head non-congruent with the container cavity, e.g. for use with different cavity shapes or when relying on rear wall stretch properties for emptying, it is preferred to design it for complete fill-out of the cavity. This can be done with a soft and adaptable ram head, e.g. for the purposes of being compatible with different cavity forms, to increase operation range or to obtain a certain emptying pattern, preferably to squeeze out the liquid from the peripheral cavity parts towards the central, axial, parts which can be done for example by making the soft ram head slightly shallower in shape than the shape of the cavity vessel form. For a single cavity form it is, however, preferred to make the ram head front surface substantially identical with the inner cavity surface or, expressed in another way, the rear surface of the front wall in the container space. The ram head can be surrounded by a support, e.g. a tube structure in which the ram head travels, which is preferably also abutted around the cavity to seal the space between ram head and cavity at least during the rear wall collapse movement, e.g. to allow high pressures or reduce leakage risks. The piston part of the ram is generally not critical to the dynamics of the ejection but rather for propulsion and will be described in connection with the actuator system.

The ram can be propelled by use of a variety of mechanisms and energy sources. The mechanism can be operated directly with manual energy, in which case, however, it is preferred to provide an leverage or gear exchange to amplify or transform force or speed, preferably towards lower speed and higher force. In order to have controlled and consistent results it is generally preferred to have automatic function in the sense that after operator triggering the propulsion takes place automatically, and preferably irreversibly, by use of stored energy. The energy may be stored in any way, e.g. in a mechanical spring, a gas spring or gas generator, as electrical energy or a combination thereof. The energy may be transmitted to the ram by suitable motor or transmission arrangements, e.g. electric motor or solenoid type motor for electrical energy, a piston and cylinder arrangement for gas springs or gas generators and rotation axis or plunger for coiled and helical springs respectively. It is generally preferred to include a transmission between the motor means and the ram proper, among other to provide a force amplification, e.g. by use of a gear wheel or a cam surface type of transmission. It is preferred that at least the ram head, and preferably parts of the ram piston, are prevented from rotation during forward movement, which can be secured by any known guiding structures, such as a non rotation symmetric part cooperation with a complementary part, the parts being positioned on ram and housing respectively. A preferred transmission component for propulsion of the ram is a screw and nut arrangement, one of which is positioned on the ram and the other on the motor side of the transmission. The necessary speed, force and movement characteristics for the ram depends on a number of conditions, such as the nature of the container parts and opening, the particular application implementation, e.g. surface or penetrative delivery, the viscosity of the preparation, e.g. aqueous solutions or ointments, etc. and general statements cannot be given. However, the energy sources, motor means and transmissions exemplified can be adapted to each need. It has also been found beneficial to include a damper, e.g. a dash pot, a linear damper, a flow valve, a magnetic damper etc., to control speed with maintained stable force. In most applications it is desirable to have a rapid rise and fall of pressure, generally requiring a stable and non-retarded speed of the ram, which is facilitated e.g. by a damper or high inertia in ram and transmission.

It is also preferred to include in the device arrangements to facilitate breakage or removal of the temporary seal over the openings as described. Although it is possible to break a seal by the pressure itself generated when collapsing the rear wall it is preferred to use an active step to break the seal. This can be done by having a de-sealing tool arranged in connection with the housing, e.g. a penetrating tool for a rupturable sealing or a wedging or drawing arrangement for removal of peelable sealing films. Such arrangements can be located at or close to the seat, e.g. to allow late action, or remote, e.g. if the seat area is crowded. The desealing tool can be operated manually or automatically or compulsory, e.g. as a part of the movement of container into the seat site. It has been found beneficial, however, to position the de-sealing tool on the rear side of the container for movement from rear to front, which allows the de-sealing tool to attack the film in the best manner possible, i.e. on the film rear side to lift it from the front wall front surface. It also allows the de-sealing tool and mechanism to be arranged more conveniently within the housing and to the rear of the container for less interference with the ejection area and ejection target but most preferably The tool can be arranged on or in connection with the ram in such a manner that it moves together with the ram, utilizing the same movement mechanism and facilitating a removal immediately before ejection and as an unavoidable part of the ejection procedure. For reasons earlier outlined the tool can preferably have a movement mechanism of its own. Preferably the de-sealing tool passes though an opening in the front wall structure, and possibly also through the rear wall, at a location not occupied by the container cavity but covered by the sealing film. With preference the dimensions of such an opening and the de-sealing tool can be mutually adapted so as to act as a guiding arrangement, as described, for final alignment of ram and cavity before activation. In operation the tool first lifts the film from the container opening and the ram head then hits the container rear wall. It is possible to perform these two steps in a single continuous movement for the ram, e.g. for simplest operation and latest possible de-sealing, or in a two-step operation, possibly requiring two triggering actions from the user, e.g. in order to enable the user to verify that the film has been properly removed. It might also be of interest to use different movements characteristics for the two steps, e.g. a slow movement for the peel not to cause tearing or rupture- and a fast action for ejection, which might require some shift arrangement, e.g. a gear shift, de-coupling of brake or damper etc. The general container design principles of the present invention strongly amplifies the above described advantages, among other by having a rigidity permitting front wall use for guiding purposes and allowing areas outside the cavity part to be utilized without instability problems.

A device as exemplified can be adapted for different uses. Depending on each application it may be beneficial to equip the device with arrangements assisting targeting and positioning. For example, when used for shooting liquid to the eye the device can have an eyecup as earlier described. Penetrating applications may require small distance or direct contact between opening and target surface, and possibly an arrangement for device triggering at a certain contact pressure of an end piece towards the target site. Larger surface treatment may require an end piece defining both an angle and a distance Method The above description has been made with reference both to structural and operational features, directly or indirectly, or follows from the descriptions made of structures, functions and objects. The invention shall be regarded to incorporate and embrace both the device and method aspects and characteristics described. The methodological aspects are not separately repeated. Method aspects will also be exemplified below in connection with the drawings. In other aspects the ejector of the invention may be used conventionally or as described in prior art.

DESCRIPTION OF DRAWINGS

FIGS. 1A to 1H depict an a device in which an on-board electric motor is used to cock a pump mechanism pump driver during retraction of a peel pin, with final indexing of its disc container, followed by forward movement of the peel pin for sensing and final removal or a temporary seal in the form of a foil over the container openings.

Figure 1A:
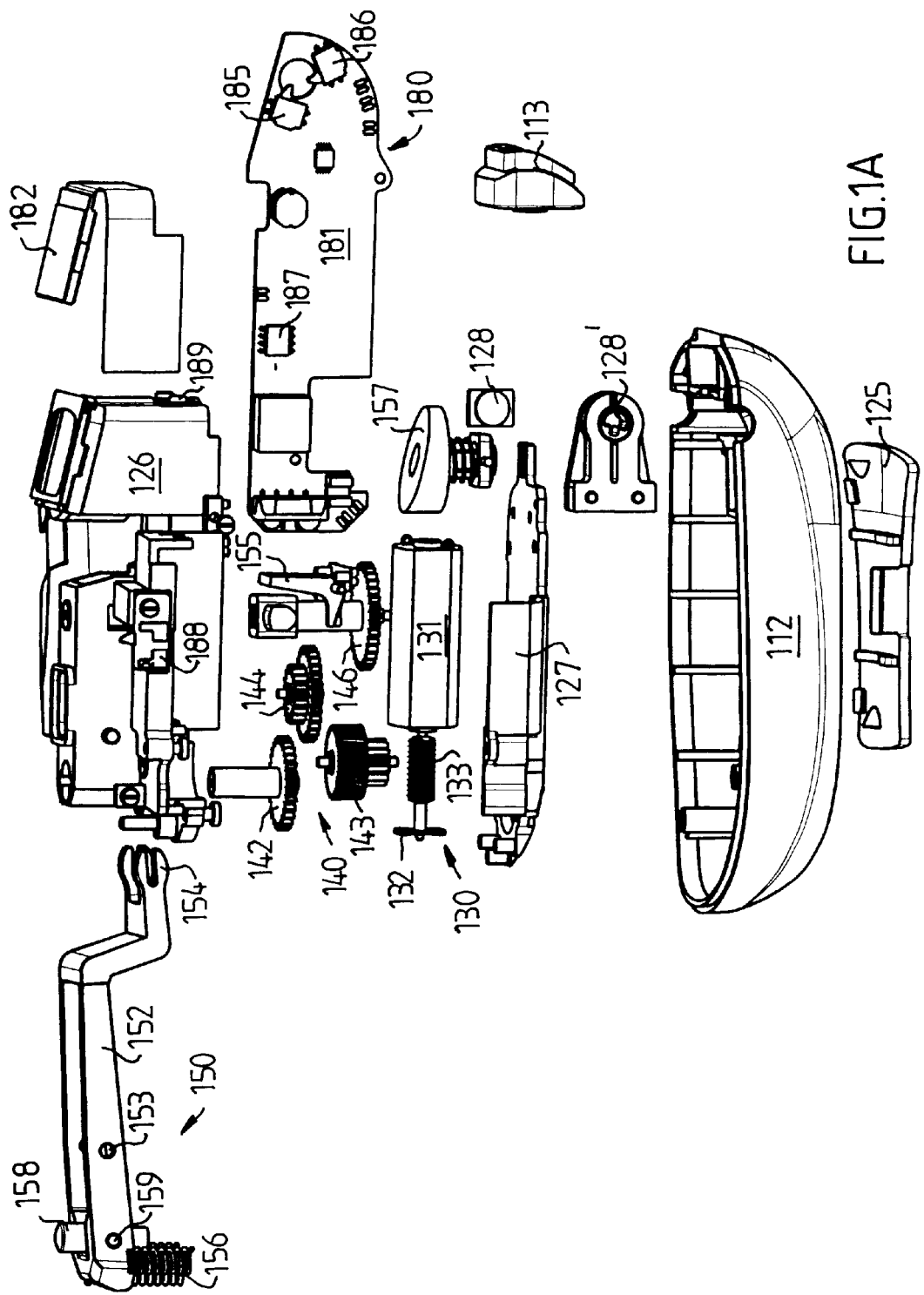
FIG. 1A shows in exploded view and FIGS. 1B to 1G the device in cross-section during five operational phases of an embodiment driven by batteries and an electric motor and utilizing a disc having a plurality of single-dose containers designed for being pressurized by a ram.
Figure 1A:
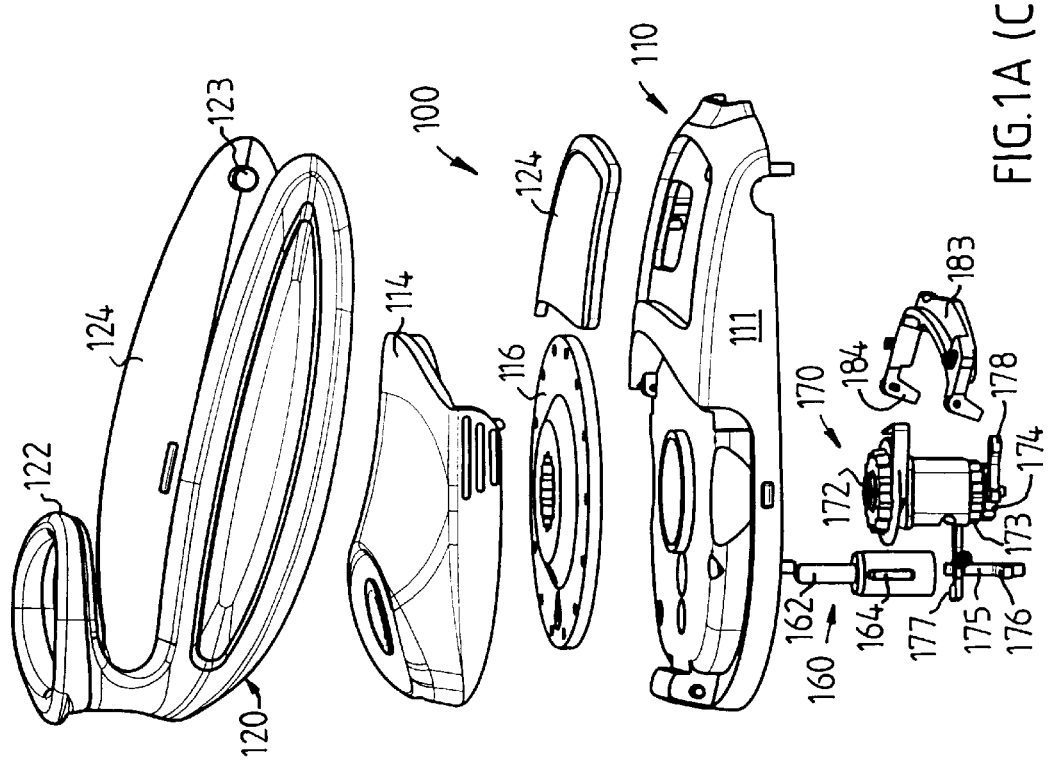

FIG. 1A shows an exploded view of the device components. The device 100 can be said to comprise a housing 110, having an upper body 111, a lower body 112, and externally accessible trigger 113. The housing also comprises a door 114, which can be opened, when the eyecup is a remote position, for insertion or replacement of disc 116 with a plurality of containers 117 with openings 118 and peel holes 119. A movable eyecup 120 comprises a rim 122 attached to arms 124 which is connected in its other end to hinge axis pins 123 supported in bearings 128 and 128', the latter having a cam part (not shown) moving with the eyecup, which cam part affects internally arranged sensors to be described. The housing further comprises a window 124 over a display and a battery closure 125.

The housing interior has a chassis upper part 126 and a chassis lower part 127 carrying the device mechanism. Said mechanism can be said to include a driving mechanism, generally designated 130, a transmission 140, a pump mechanism 150 with arrangement for stored cocking energy, a peel mechanism 160, an indexing mechanism 170 and a control system 180, including a board 181 for electronics.

The driving mechanism 130 can be said to include the motor 131 with batteries (not shown) having a rotating shaft with a front encoder 132 for counting of motor revolutions and an external screw-thread 133 for cooperation with the upstream gear wheel in the transmission chain. The motor and detectors for motor revolutions are attached to the electric board 181.

The transmission 140 can be said to comprise a set of gear wheels in a gear train arranged to gear down motor speed and increase force in adaptation to each function. A peel wheel 142 is arranged to drive the peel mechanism, intermediate wheels 143 and 144 are parts of the gear trains without any further function and a cocking wheel 146 is arranged to drive the cocking mechanism for the pump mechanism. See also FIG. 1H for details.

The pump mechanism 150 can be said to include a lever 152, which can rotate around a lever axis 153 allowing its end at the eyecup end of the housing to move up and down. At the other end of the lever is a damper attachment 154. The damper attachment is connected to a piston part of a damper 157, the cylinder part of which is arranged stationary. In this arrangement the piston is moved against vacuum and bleeding of air into the cylinder, for retarding the speed of the ram impact. The pump mechanism includes a ram 158 rotationally connected to the lever at 159 and guided in the chassis, allowing the ram to attack the container deformable rear wall in a substantially straight movement. Downwards movement, away from the eyecup in the shown position, of the lever 152 is used to cock springs 156 in the pump mechanism. The cock springs are arranged to throw the ram upon release towards the container 117 to eject liquid through the openings 118. As best seen in FIG. 1H, the lever has a nut 151, with internal screw-threads (not shown), for cooperation with corresponding threads associated with a screw, with external threads, rotating together with the cocking wheel 146 in the transmission. The nut is attached to the lever, allowing movement of the lever up and down depending on motor direction. The nut is attached to the lever to catch it only in the cocking direction, not in the release direction. A spring biased L-shaped ram lock 155 is arranged to go under the lever 152, when in the cocked position, to keep it there until release. After motor reversal the nut may then move free from the lever in the release direction until it hits the lower leg in the L-shape, which will release the ram lock and throw the ram, and this will happen when the peel pin 162 has reached about its most forward position and accordingly completed peeling.

The peel mechanism can be said to include the peel pin 162, which is keyed at 164 to the chassis to prevent its rotation, and has internal threads 166 for cooperation with external threads on peel wheel 142 to allow its movement up or down by the motor. It is clear that in this embodiment the motor and transmission drives the peel pin directly and not by cocking springs or similar energy storage. At the end of the forward peeling movement the pump mechanism is activated to throw the ram by release of the ram lock 155 in the manner described above. At the rear side of the peel wheel 142 is a force sensitive sensor 168 arranged to switch at a certain counter-force from the resistance force the peel pin has to overcome when the temporary seal foil is torn away, which allows the control system to verify its presence.

The indexing mechanism 170 comprises an index wheel 172, for cooperation with the correspondingly shaped container disc hub, with teeth corresponding to an equal number of containers on the disc. The index wheel has certain mobility and is spring loaded to facilitate connection to the disc. At the other end of the index wheel are toothed inner catch wheel 173 and outer catch wheel 174. An increment arrangement is driven by the peel pin 162 keys 164, which on rearward movement affects a tapered surface 176 of an axial lever 175, which in turn affects a radial lever 177, which is in hook contact with inner catch wheel 173, to turn the index wheel one tooth. A counter lever 178 is in spring biased hook contact with outer catch wheel to prevent the index wheel from rotating in the opposite direction. The indexing correspond to one tooth after ejection in each operation cycle and lines up a fresh container with the ram. This is an incremental action initiated when the peel pin during its rearward movement arrives at a remote position relative the eyecup part of the device, in which position the pin has been withdrawn from disc peel hole to enable its rotation. This action is also sensed by a counter sensor (not shown), which is used by the processor on the board 181 to decrement the displayed number of remaining doses figure on the display. The processor is also arranged prevent triggering after all doses of the disc being ejected or if a defect container has been detected, then moving the peel pin to its rearmost position, which triggers opening of the door for disc replacement.

As indicated most electronic components are positioned on the electronic board 181. In addition to the features mentioned the control system 180 can be said to include the display 182, also connected to the board, and a door locker 183 with arms 184 affecting a door sensor 188 depending on the door position Further, sensors 185 and 186 cooperates with the mentioned cam surfaces in bearing 128' for detection of eyecup position. A switch 189 is arranged on the chassis upper part 126 to be affected by the trigger 113. A processor 187 is arranged for operation of the device.

Figure 1B:
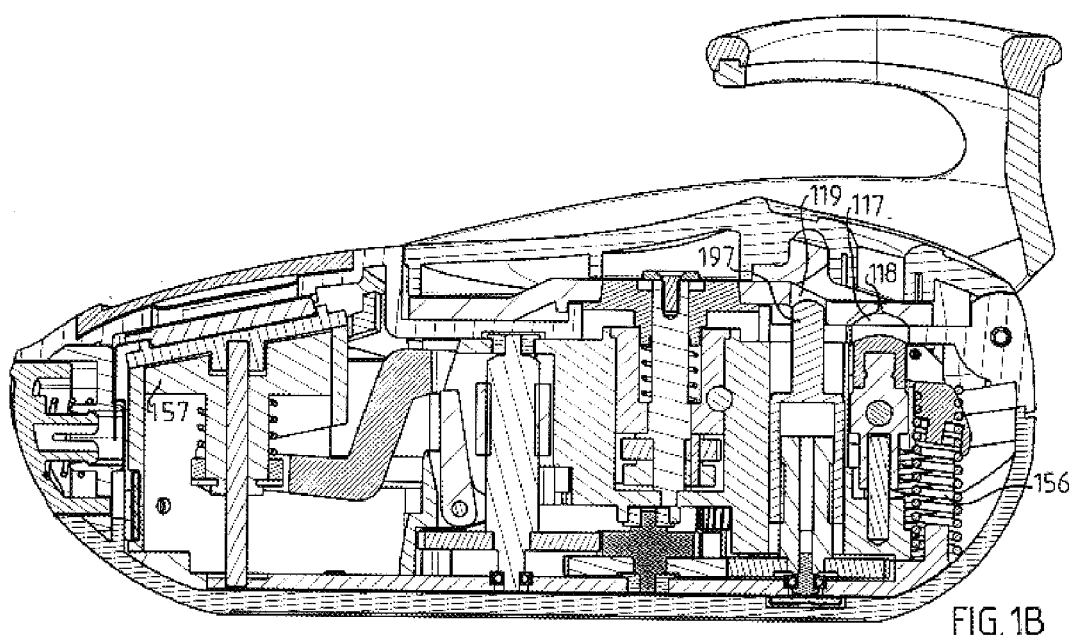
FIG. 1H shows in greater detail the components of the main lever.
Figure 1C:
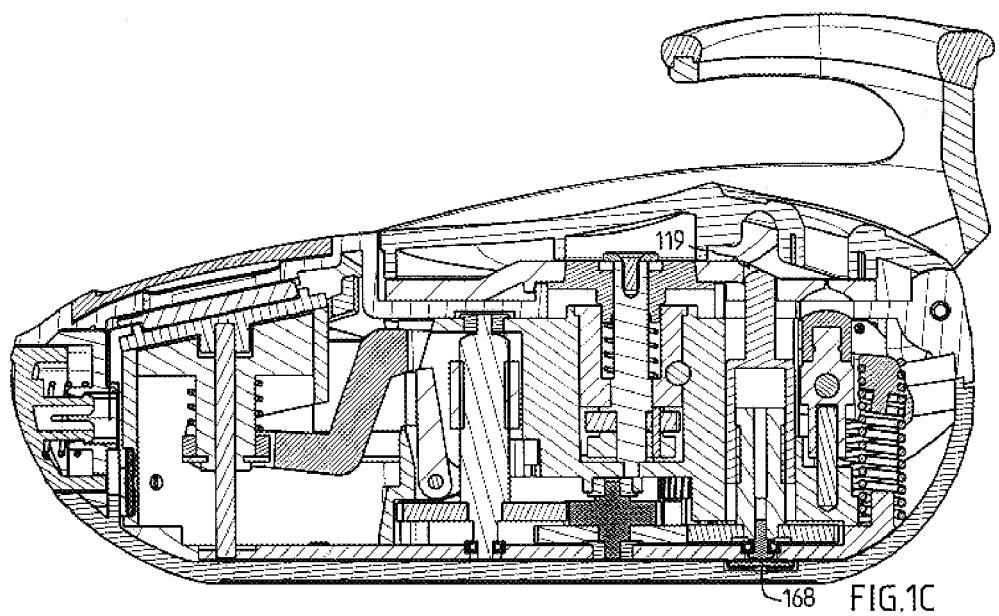

FIGS. 1B to 1F show the various phases of the device operation. FIG. 1B corresponds to a Standby position, immediately before an ejection cycle. The peel pin 162 is in an intermediate position immediately to the rear of the foil to be removed. It should be noted that the cock springs 156 are already in a cocked state, which cocking has taken place earlier during a rearward movement of the peel pin, and the damper 157 is in its initial position. In the Touch foil position shown in FIG. 1C the trigger has been activated and the motor has moved the peel pin a small distance forwards to the point where it has penetrated the peel hole 119 in the disc and touches on the foil to verify its presence via sensor 168. In the Peel off position of FIG. 1D the peel pin 162 has completed its forward movement and removed the foil. In the Injection position of FIG. 1E, at the forward extreme for the peel pin, the ram lock 155 has been released, which has triggered the ram 158, which has completed the ejection in the position shown. The lever 152 has moved up to the right in the Figure, under influence of the cock springs 156, and down to the left under withdrawal of the damper 157 piston. In the Start index position of FIG. 1F the device has been re-cocked during return movement of the peel pin, by again reversing the motor and the peel pin in a more rearward position than in FIG. 1B in which indexing of the disc is initiated during further rearward movement of the peel pin. During the late part of this rearward movement for the peel pin indexing of the disc will be completed. By again reversing the motor the peel pin can be moved forwards to the Standby position shown in FIG. 1B. In this position the device is ready for a new ejection cycle if the trigger 113 is pressed and if the eyecup 120 is in the shown active position. Alternatively, as shown in the Open cover position of FIG. 1G, the processor may move the peel pin to a still more rearward position than in the Start index position shown in FIG. 1F, which will release the mechanical lock for the door 114 in order to allow disc replacement, which will also require that the eyecup is swung to a remote position about 180 degrees from the position shown. This will happen if all containers of the disc have been used or if a fault has been detected.

Figure 1D:
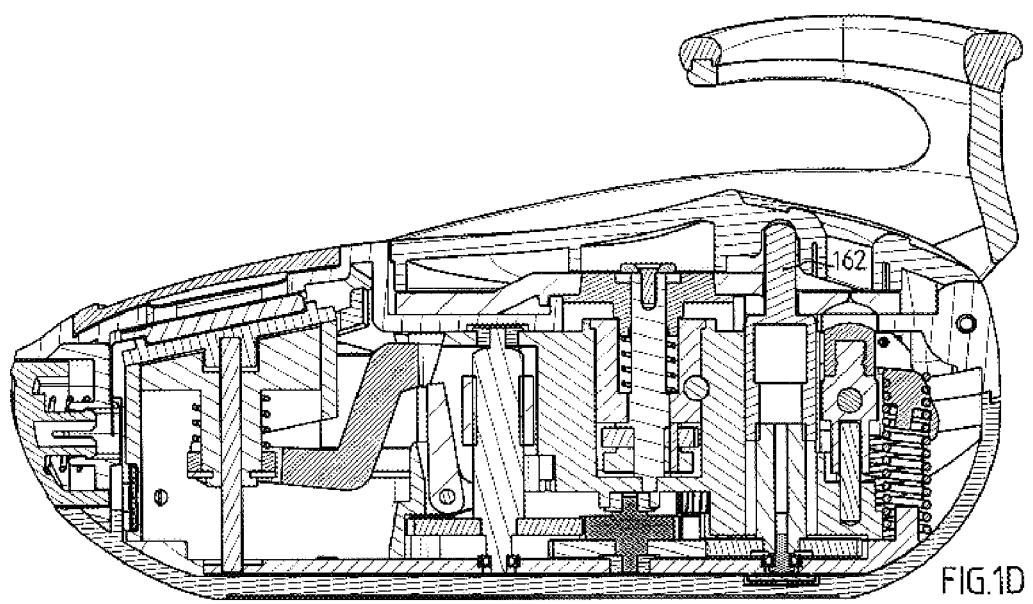
Figure 1E:
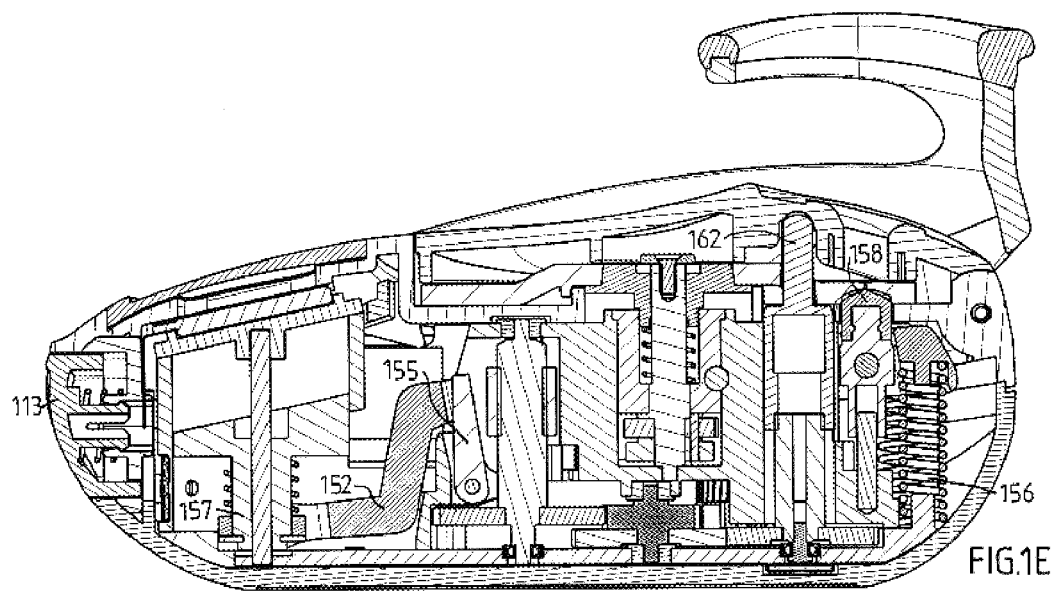
Figure 1F:
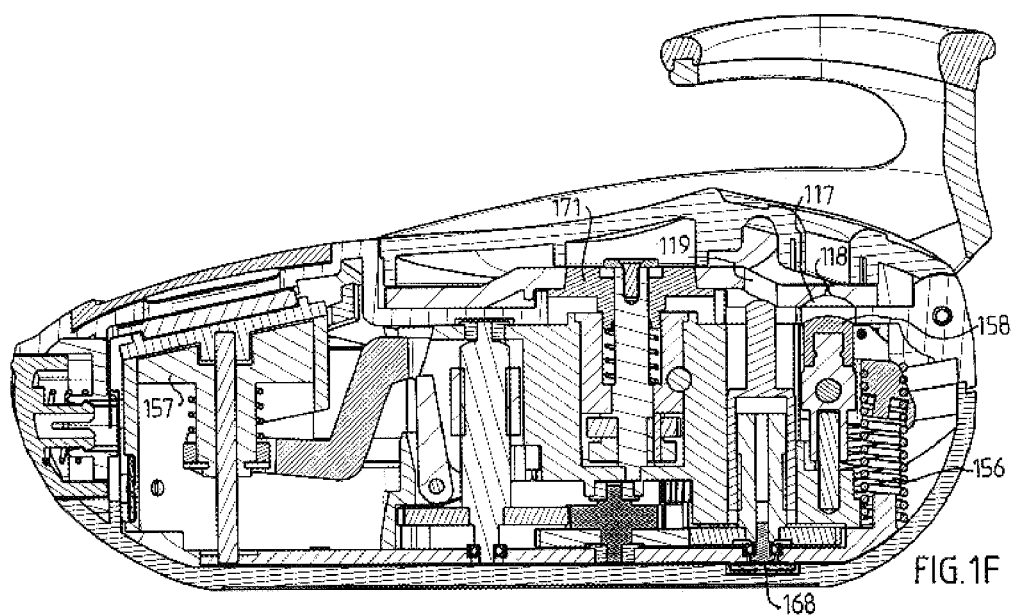
Figure 1G:
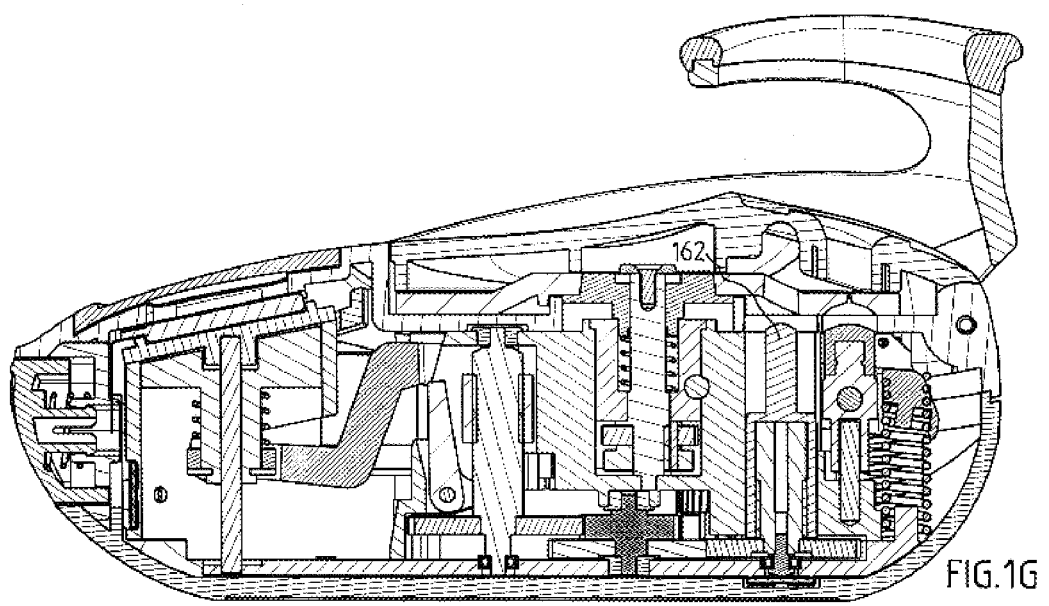

Use of the device will be described from a start position in which the device is in the Standby position as shown in FIG. 1B. If the eyecup is in the rest position (not shown) it need to be moved to the shown active position to activate the device. The display may show an alert signal, e.g. by flashing. The eyecup is placed against the eye and the trigger activated, which is only possible with the eyecup in the active position, and this will initiate a full sequence of peeling, ejection and indexing in a compulsory manner by the actions described above until the device is again in the state of FIG. 1B. Alternatively the trigger activation will only make the device proceed to full peeling of the foil as illustrated in FIG. 1D. Then a new trigger action will be needed to complete ejection as shown in FIG. 1E and automatically proceed to full completion as illustrated in FIG. 1B or to the Open cover position of FIG. 1G. The second triggering shall be made within a certain time frame from the first triggering, otherwise the processor will automatically proceed to end and the dose is lost. This in order to not risk container contamination after opening. When all doses have been consumed the processor will activate the motor to drive the peel pin to its rearmost position as shown in FIG. 1G for disc replacement. After detection of a fresh disc the processor will move the peel pin to the Standby position shown in FIG. 1B and the doses counter will be reset.

Figure 2A:
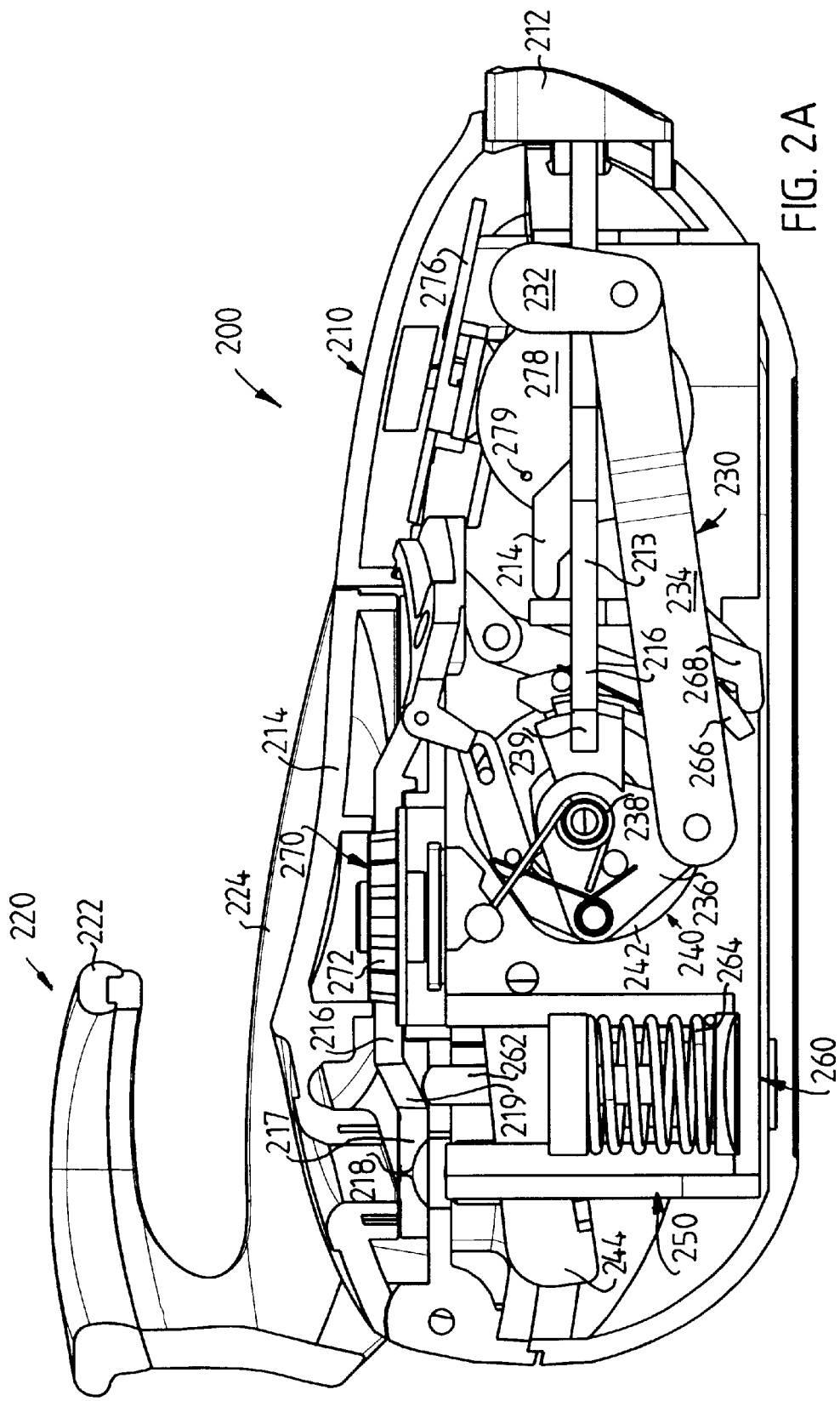
FIGS. 2A to 2C show schematically in an open view and in two cross-sections respectively an alternative embodiment of an entirely mechanical device which is arranged to be cocked by manual energy.
Figure 2B:
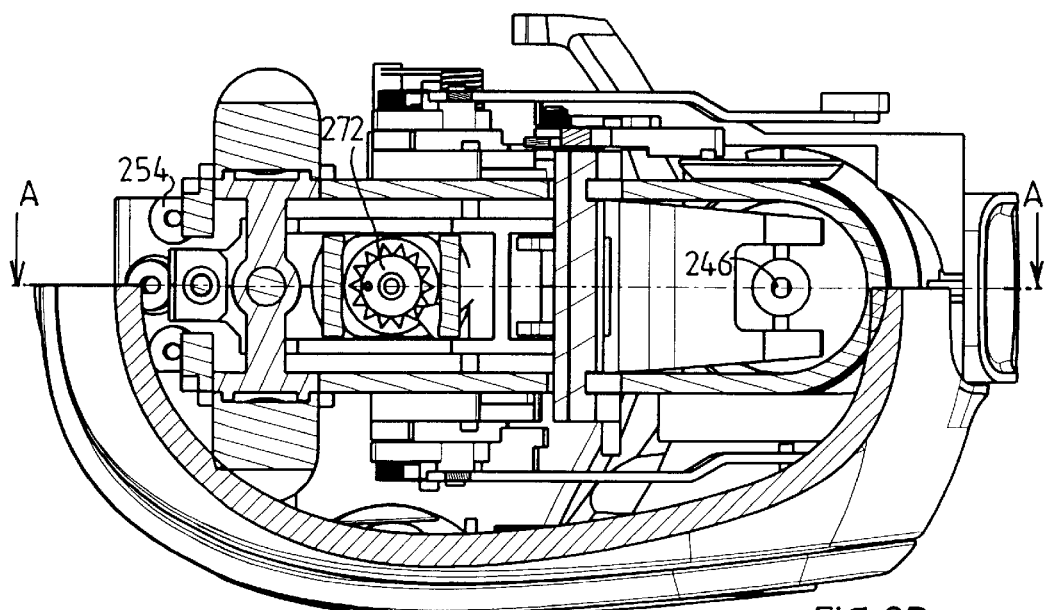
Figure 2C:
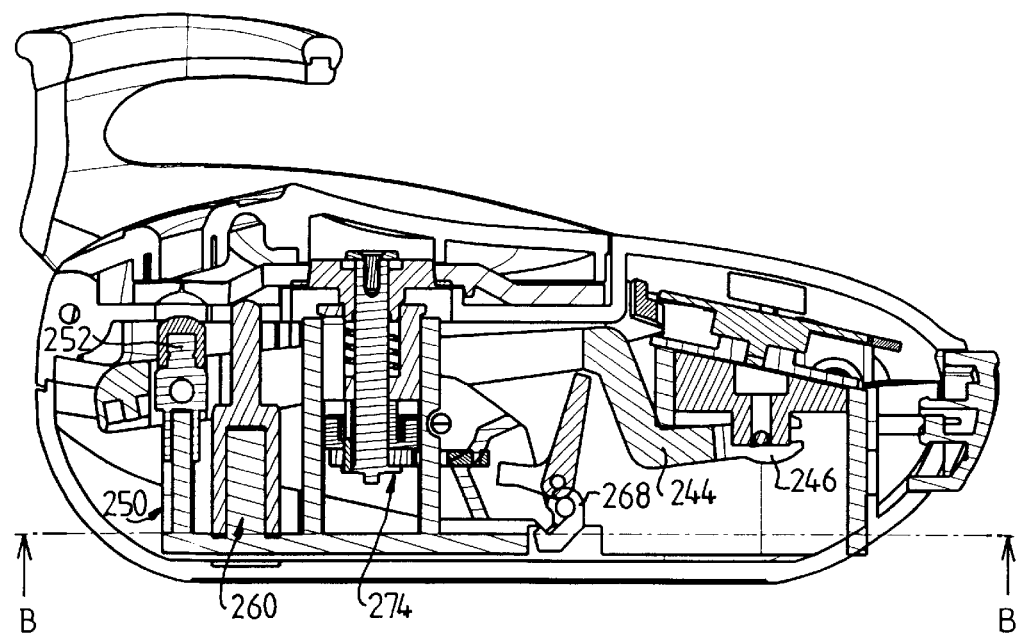

FIGS. 2A to 2C depict an overview of a modified device as compared to that of FIG. 1 and the following description will mainly focus on the differences. The FIG. 2 device is entirely mechanical and is arranged to be operated by manual energy, which is imputed to the device by manually pressing the eyecup from a remote position relative to the housing towards a close position and energy is stored as cocking energy within springs in the device. In FIG. 2 the device is shown in active state before ejection, i.e. after manual energy has been inputted and the eyecup is in its active position ready for ejection.

The device 200 can be said to comprise a housing 210, having an externally accessible trigger 212 connected to a start pin 214 and lock pin 213. The housing also comprises a door 214, which can be opened, when the eyecup is a remote position, for insertion or replacement of disc 216 with a plurality of containers 217 with openings 218 and peel holes 219. An eyecup 220 comprises a rim 222 attached to an arm 224 which is connected in its other end to a hinge with a rotating axis penetrating into the housing and being connected to its mechanism. Said mechanism can be said to include a driving mechanism, generally designated 230, a cocking mechanism 240, a pump mechanism 250, a peeling mechanism 260, an indexing mechanism 270 and a control system 280.

The eyecup arm is connected to a partial wheel 232 of the driving mechanism, which via a "locomotive" link 234 positively transmit the same rotation to driver wheel 236. The driver wheel is connected to a cocking wheel 242 of the cocking mechanism 240 via a freewheel system 238, arranged to allow concurrent rotation of the wheels when cocking the device by pressing the eyecup towards the housing but freeing the cocking wheel from the driving wheel when at opposite rotation. The driving wheel has an extension with a slot 239 arranged for cooperation with the lock pin 213 of the trigger so that the trigger, and accordingly the eyecup, can be pushed when the driver wheel is flush with the slot, which appears when the eyecup is in the active position, but not when the lock pin is at the extension outside the slot.

The cocking wheel 242 of the cocking mechanism is connected to a lever 244, which can rotate around a lever hinge (not shown) as in the FIG. 1 embodiment end, allowing its eyecup end to move up and down. The lover other end 246 is connected to a damper as in FIG. 1. Downwards movement, away from the eyecup in the shown position, of the lever 244 is used to cock separate springs in the pump mechanism and the peeling mechanism.

The pump mechanism 250, substantially symmetrical around the device midline, includes a ram 252 and the pump springs 254, arranged to throw the ram upon release towards the container 217 to eject liquid through the openings 219.

The peel mechanism 260, also substantially symmetrical around the device midline, similarly includes a peel pin 262 and the peel springs 264, arranged to throw the pin, upon release, towards the disc 216 to make the pin penetrate through the peel holes 219 of the disc to thereby remove the temporary seal film. The release takes place when a transmission hook 266 is freed by action of the trigger 212 via the start pin 214 and an intermediate transmission rocker 268. When this happens the cocking wheel is enabled for rotation in the opposite direction as compared to the cocking movement. At the end of the peeling movement the pump mechanism is activated to throw the ram.

The indexing mechanism 270 comprises an index wheel 272, for cooperation with the correspondingly shaped container disc hub, here shown with 14 teeth corresponding to an equal number of containers on the disc. The index wheel is connected to an increment arrangement 274, arranged to rotate the index wheel and disc an angle corresponding to one tooth. This is an incremental action initiated when the peel pin during cocking of the device arrives at its most remote position relative the eyecup part of the device, in which position the pin has been withdrawn from disc peel hole to enable its rotation. This action is also transmitted to a counter disc 276, which is also incremented to show a new remaining doses figure in a housing window and also to a gear wheel 278, which is given an incremental rotation. The gear wheel has a bolt 279, which after 14 doses ejected goes into contact with the transmission rocker 268 to relieve the transmission hook from the driver wheel, hereby enabling eyecup movement to a remote position beyond the active position, in turn allowing opening of the door for disc replacement.

Use of the device will be described from a start position in which the device is cocked with the eye-cup in the close rest position, where the trigger cannot be pressed due to the lock pin 213 being outside the slot 239. The eyecup is moved to the active position where the trigger can be pressed. The eyecup is placed against the eye and the trigger activated which will initiate a full sequence of peeling, ejection and indexing in a compulsory manner by the actions described above. Upon release of the trigger the driver wheel 236 is freed thereby the eyecup and the springs associated with the driver wheel will move the eyecup automatically to a remote position about 30 degrees out from the housing to urge the user to perform a cocking movement on the eyecup. The user pushes the eyecup to the close rest position, which cocks the device and at the end of the sequence also indexes the disc and increments the counter. The eyecup is locked in the rest position until it is actively moved to the active position for a repeated cycle. If 14 doses has been taken the eyecup is not locked but can be moved to a remote position where the door can be open for disc replacement.

The invention is not limited to the embodiments described and illustrated but can be varied within the scope of the patent claims.

What is claimed is:

1. A device for ejecting a liquid stream towards an eye, the stream moving from a proximal position towards a distal position, the device comprising a) a housing, b) a container for the liquid, c) at least one opening arranged for ejection of the stream and being in fluid communication with the container, d) a pump mechanism operable to deliver at least part of the liquid from the container through the opening to form the stream, e) an eyecup with a contact surface arranged for contact with the eye or its facial surroundings, wherein the eyecup is arranged movable with respect to the opening or housing between at least two positions comprising i) an active position with said eyecup contact surface at a defined safety distance to the opening, and ii) a rest position with the eyecup contact surface at a position more proximal than in the active position, and f) a sensor adapted to allow discrimination between the positions.

2. The device of claim 1, wherein the opening is arranged fixed with respect to the housing when moving the eyecup.

3. The device of claim 1, wherein the container is removably attached to the housing.

4. The device of claim 1, wherein a plurality of single-dose containers are connected and arranged to be moved sequentially into an operative position relative to the pump mechanism.

5. The device of claim 1, wherein the eyecup is arranged to allow movement to at least one further position farther away from the housing or opening than the active position.

6. The device of claim 1, wherein the eyecup is entirely removable from the housing.

7. The device of claim 1, wherein the eyecup is arranged to move with a translational movement.

8. The device of claim 1, wherein the eyecup is arranged to be moved with a rotational component.

9. The device of claim 8, wherein the eyecup is connected to the housing via a hinge.

10. The device of claim 1, wherein the sensor system is adapted to generate at least one signal and the device is adapted to perform at least one action on the basis of the signal, directly or after processing into a control signal.

11. The device of claim 10, wherein the signal generation or processing comprises at least one mechanical step.

12. The device of claim 10, wherein the signal generation or processing comprises at least one electromagnetic step.

13. The device of claim 10, wherein the sensor is adapted to generate a signal representative for continuous eyecup positions.

14. The device of claim 10, wherein the device is adapted to generate a signal representative for discrete eyecup positions.

15. The device of claim 1, wherein the device is adapted to deliver at least one message detectable by a user on the basis of the signal.

16. The device of claim 1, wherein the device is adapted to perform at least one operation step of the device.

17. The device of claim 15, wherein the signal is adapted to enable or disable the pump mechanism.

18. The device of claim 15, wherein the device is adapted to only be triggered when the eyecup is in the active position.

19. The device of claim 15, wherein the signal is adapted to disable or enable an initiation action for the container.

20. The device of claim 15, wherein the signal is adapted to enable or disable a device control action.

21. The device of claim 15, wherein the signal is adapted to enable or disable a device door.

22. The device of claim 1, wherein the eyecup is arranged movable with respect to the opening.

23. The device of claim 1, wherein the eyecup is arranged movable with respect to the housing.

24. A method for operating an ejection device to eject a liquid stream, the stream moving from a proximal position towards a distal position, the device comprising a) a housing, b) a container for the liquid, c) at least one opening arranged for ejection of the stream and being in fluid communication with the container, d) a pump mechanism operable to deliver at least part of the liquid from the container through the opening to form the stream, e) a part arranged to define a predetermined distance to a target and arranged movable with respect to the opening or housing between at least two positions comprising i) an active position with said part at a defined safety distance to the opening, and ii) a rest position with the part at a position more proximal than in the active position, and f) a sensor adapted to allow discrimination between the positions, the method comprising moving the part between the active position and the rest position or vice versa, generating a signal representative for either the active position or the rest position, optionally processing the signal to obtain a control signal, and using the signal or control signal to perform at least one action on the container, the opening, the pump mechanism or the part.

25. A device for ejecting a liquid stream, the stream moving from a proximal position towards a distal position, the device comprising a) a housing, b) a container for the liquid, c) at least one opening arranged for ejection of the stream and being in fluid communication with the container, d) a pump mechanism, including a pump driver able to store cocked energy for driving the pump mechanism, operable to deliver at least part of the liquid from the container through the outlet to form the stream, e) at least one activation mechanism operable, separately from the pump mechanism, to initiate the device for the liquid delivery, and f) a driving mechanism adapted to transform manual or stored energy both i) into cocked energy of the pump driver, and ii) into direct or stored energy for operation of the activation mechanism.

26. The device of claim 25, comprising one or more mechanical springs adapted to store at least part of the cocked energy.

27. The device of claim 25, wherein the driving mechanism is adapted to receive manual energy.

28. The device of claim 25, wherein the driving mechanism is adapted to receive stored energy.

29. The device of claim 25, wherein the stored energy comprises electrical energy.

30. The device of claim 25, wherein the driving mechanism comprises a transmission.

31. The device of claim 30, wherein the transmission is adapted to perform gear down from lower to higher force.

32. The device of claim 25, wherein the activation mechanism is adapted to drive an indexing action in which a container is brought into operative relationship with the pump mechanism.

33. The device of claim 25, wherein the activation mechanism is adapted to drive a peeling action in which a temporary seal is removed from the container.

34. The device of claim 33, wherein the peeling action comprises moving a de-sealing tool through a disc member having a plurality of containers.

35. The device of claim 34, wherein the peeling action includes control of presence of a temporary seal before its removal.

36. The device of claim 25, wherein the driving mechanism is adapted to cock stored energy for driving the activation mechanism.

37. The device of claim 25, wherein the driving mechanism is adapted to cock stored energy for driving the activation mechanism directly.

38. The device of claim 25, wherein the driving mechanism is adapted to drive the cocking and activation mechanism at least partly in sequence.

39. The device of claim 38, wherein the activation mechanism is adapted to drive at least two actions at least partially in sequence.

40. The device of claim 25, wherein the activation mechanism is adapted to drive a control step and/or an initiation step for the container or the opening.

41. The device of claim 25, wherein the device further comprises an eyecup with a contact surface arranged for contact with the eye or its facial surroundings.

42. A method for operating an ejection device for ejecting a liquid stream, the stream moving from a proximal position towards a distal position, the device comprising a) a housing, b) a container for the liquid, c) at least one opening arranged for ejection of the stream and being in fluid communication with the container, d) a pump mechanism, including a pump driver to store cocked energy for driving the pump mechanism, operable to deliver at least part of the liquid from the container through the outlet to form the stream, and e) at least one activation mechanism operable, separately from the pump mechanism, to initiate the device for the liquid delivery, the method comprising operating a driving mechanism to transform manual or stored energy both i) into cocked energy of the pump driver, and ii) into direct or stored energy for operation of the activation mechanism.

* * * * *